(12) United States Patent
Ollivier et al.

(10) Patent No.: US 10,144,977 B2
(45) Date of Patent: Dec. 4, 2018

(54) HYPERHALOPHILIC STRAIN AND USE THEREOF FOR THE DEGRADATION OF CARBON-CONTAINING SUBSTRATES

(71) Applicants: Institut De Recherche Pour Le Developpement (I.R.D.), Marseilles (FR); Societe Interoleagineuse D'Assistance et de Developpement (SIA), Paris (FR)

(72) Inventors: Bernard Ollivier, Roquevaire (FR); Wajdi Ben Hania, Marseilles (FR); France Thevenieau, Chartres (FR); Abdeljabbar Hedi, Tunis (TN); Marie-Laure Fardeau, Les Pennes Mirabeau (FR)

(73) Assignees: Institut de Recherche Pour le Developpement (I.R.D.), Marseille (FR); Societe Interoleagineuse D'Assistance et de Developpement (SIA), Paris (FR)

( * ) Notice: Subject to any disclaimer, the term of this patent is extended or adjusted under 35 U.S.C. 154(b) by 0 days.

(21) Appl. No.: 15/308,457

(22) PCT Filed: Apr. 30, 2015

(86) PCT No.: PCT/EP2015/059609
§ 371 (c)(1),
(2) Date: Nov. 2, 2016

(87) PCT Pub. No.: WO2015/176940
PCT Pub. Date: Nov. 26, 2015

(65) Prior Publication Data
US 2017/0058368 A1    Mar. 2, 2017

(30) Foreign Application Priority Data
May 2, 2014   (EP) .................... 14305655

(51) Int. Cl.
| | |
|---|---|
| *C12P 7/62* | (2006.01) |
| *C08G 63/06* | (2006.01) |
| *C12R 1/00* | (2006.01) |
| *C12R 1/01* | (2006.01) |
| *C12N 1/06* | (2006.01) |

(52) U.S. Cl.
CPC .................. *C12R 1/00* (2013.01); *C12N 1/06* (2013.01); *C12P 7/625* (2013.01); *C12R 1/01* (2013.01)

(58) Field of Classification Search
CPC .................... C12P 7/62; C08G 63/06
See application file for complete search history.

(56) References Cited

FOREIGN PATENT DOCUMENTS

| | | |
|---|---|---|
| EP | 2202316 | 6/2010 |
| WO | 2009156950 | 12/2009 |

OTHER PUBLICATIONS

Al-Mailem et al., Extremophiles, 14 (3), 321-328, 2010.*
Hermann-Krauss, Carmen et al.: "Archaeal production of polyhydroxyalkanoate (PHA) Co-and Terpolyesters from Biodiesel Industry-Derived By-Products," Archaea, Jan. 1, 2013, vol. 2013; pp. 1-10.
Simon-Colin, C. et al: "*Halomonas profundus* sp. nov., a new PHA-producing bacterium isolated from a deep-sea hydrothermal vent shrimp," Journal of Applied Microbiology, 2008, vol. 104:1425-1432.
Chen, C. Will: "Enzymatic extruded starch as a carbon source for the production of poly(3-hydroxybutyrate-co-3-hydroxyvalerate) by Haloferax mediterranei," Process Biochemistry, 2006, vol. 41:2289-2296.
Pramanik, Amab et al.: "Utilization of vinasse for the production of polyhydroxybutyrate by Haloarcula marismortui," Folia Microbiol, 2012, vol. 57: 71-79.
Lopez-Cuellar, M.R. et al.: "Production of polyhydroxyalkanoates (PHAs) with canola oil as carbon source," International Journal of Biological Macromolecules, 2011, vol. 48:74-80.
Singh, Akhilesh K. and Nirupama Mallick: Exploitation of inexpensive substrates for production of a novel SCL-LCL-PHA copolymer by Pseudomonas aeruginosa MTCC 7925, J Ind Microbiol Biotechnol, 2009, vol. 36:347-354.
De Ley, J. et al., "The quantitative measurement of DNA hybridization from renaturation rates," Eur. J. Biochem., 1970, vol. 12:133-142.
Huss, Volker A.R., et al., "Studies on the spectrophotometric determination of DNA hybridization from renaturation rates," System. Appl. Microbiol., 1983, vol. 4:184-192.
Lillo, Jose Garcia and Francisco Rodriguez-Valera: "Effects of culture conditions on poly(β-hydroxybutyric acid) production by Haloferax mediterranei," Applied and Environmental Microbiology, Aug. 1990, vol. 56, No. 8:2517-2521.

* cited by examiner

*Primary Examiner* — Maryam Monshipouri
(74) *Attorney, Agent, or Firm* — Cuenot, Forsythe & Kim, LLC

(57) ABSTRACT

The present invention relates to a novel hyperhalophilic strain and use thereof for the degradation of carbon-containing substrates, in particular making it possible to prepare novel polymers.

17 Claims, 3 Drawing Sheets

HYPERHALOPHILIC STRAIN AND USE THEREOF FOR THE DEGRADATION OF CARBON-CONTAINING SUBSTRATES

CROSS REFERENCE TO RELATED APPLICATIONS

The present application is the U.S. national phase under 35 U.S.C. 371 of international patent application number PCT/EP2015/059609 filed on Apr. 30, 2015, which designated the U.S.

FIELD OF THE INVENTION

The present invention relates to a novel hyperhalophilic strain and the use thereof for the degradation of carbon-containing substrates, in particular making it possible to prepare novel polymers.

BACKGROUND

Every day, thousands of tonnes of petroleum-derived plastic waste accumulate in the environment, leading to an increasing number of landfill sites for non-biodegradable waste and escalation of the costs of waste disposal.

One solution to this problem is to use biodegradable alternatives to these plastics, one of which is the production of polyhydroxyalkanoates (PHA), a class of high-performance biodegradable polymers.

PHAs can be produced commercially in processes of intracellular storage (reserves) carried out by microorganisms using a suitable substrate (in particular a sugar or an organic acid). However, the cost of the PHAs thus obtained is well above that of the petroleum-derived plastics, in particular because of the strict environmental controls required and the sterile operating conditions required for controlling the production operation.

Moreover, PHAs do not always have the necessary physical characteristics for specific industrial applications, in particular glass transition temperature (Tg) or transparency.

*Haloferax* is a genus of Archaea belonging to the phylum *Euryarchaeota* and to the order *Halobacteriales*. The cells of *Haloferax* are pleomorphic motile rods or flattened disks, and are strict aerobes. They are hyperhalophilic organisms.

Certain species of *Haloferax* produce biopolymers. In particular, *Haloferax mediterranei* produces PHA (Lillo et al. Appl. Environ. Microb. 56:2517-2521, 1990).

However, Lillo et al. describe that *Haloferax mediterranei* only produces PHA under conditions of stress, from starch or glucose, and not from other carbon-containing substrates such as oils, triglycerides, fatty acids or glycerol.

SUMMARY

Thus, a purpose of the present invention is to provide a novel hyperhalophilic microorganism capable of degrading substrates such as oils, triglycerides, fatty acids, alkanes, co-products from oil refineries, glycerol, or derivatives thereof, said microorganism in particular being genetically unmodified, and having the ability to grow in a non-sterile medium.

Another purpose of the present invention is to provide a novel hyperhalophilic microorganism capable of degrading substrates such as oils, triglycerides, fatty acids, alkanes, co-products from oil refineries, glycerol, or derivatives thereof, in particular making it possible to prepare PHA.

Another purpose of the present invention is to provide a novel hyperhalophilic microorganism capable of producing a PHA of high molecular weight and/or of high transparency.

Another purpose of the present invention is to provide a novel hyperhalophilic microorganism capable of producing PHA even under normal culture conditions, i.e. without stress.

The invention consequently relates to the use of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, for implementing a method for the degradation:

of a substrate constituted by or comprising a product or co-product from the refining of oil producing plants or liquid hydrocarbons, and optionally of a carbon-containing co-substrate, contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation:

of a substrate constituted by or comprising a product or co-product from the refining of oil producing plants or liquid hydrocarbons, and optionally of a carbon-containing co-substrate, contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation of a substrate constituted by or comprising a product or co-product from the refining of oil producing plants or liquid hydrocarbons, in the absence of a carbon-containing co-substrate, contained in the culture medium of said aerobic hyperhalophilic strain.

By "product or co-product from the refining of oil producing plants or liquid hydrocarbons" in particular is meant oils, triglycerides, fatty acids, glycerol, alkanes, alkenes, polyenes, derivatives thereof, as well as compositions comprising them.

By "liquid hydrocarbons" is meant hydrocarbons that are liquid at ambient temperature and at atmospheric pressure.

By "percentage DNA-DNA hybridization" is meant the percentage similarity between two genomes of microorganisms.

DNA/DNA hybridization was carried out between the strain S3S1 and the strain *Haloferax mediterranei*, according to the following conditions.

The percentage DNA-DNA hybridization is, for example, determined by the German Collection of Microorganisms and Cell Cultures (DSMZ) by the method described by De Ley et al. (De Ley, J., Cattoir, H. & Reynaerts, A. (1970). The quantitative measurement of DNA hybridization from renaturation rates. *Eur J Biochem* 12, 133-142) and modified by Huss et al. (Huss, V. A. R., Festl, H. & Schleifer, K. H.

(1983). Studies on the spectrophotometric determination of DNA hybridization from renaturation rates. *Syst Appl Microbiol* 4, 184-192).

In particular, the percentage DNA-DNA hybridization is determined using a UV/VIS spectrophotometer (Cary 100 Bio model) equipped with a Peltier-thermostated 6×6 multicell changer and a temperature controller with an in-situ temperature sensor (Varian).

The invention also relates to the use of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, for implementing a method for the degradation:
of a substrate constituted by or comprising an element selected from triglycerides, by-products thereof, alkanes, alkenes, polyenes and mixtures thereof;
and optionally of a carbon-containing co-substrate,
contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of anaerobic hyperhalophilic strain being such that the percentage DNA-DNA hybridization between this aerobic hyperhalophilic strain and strain S3S1 is at least 90%, in particular at least 92%, for implementing a method for the degradation:
of a substrate constituted by or comprising an element selected from triglycerides, by-products thereof, alkanes, alkenes, polyenes and mixtures thereof;
and optionally of a carbon-containing co-substrate,
contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation:
of a substrate constituted by or comprising an element selected from triglycerides, by-products thereof, alkanes, alkenes, polyenes and mixtures thereof, in the absence of a carbon-containing co-substrate,
contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, for implementing a method for the degradation:
of a substrate constituted by or comprising a product or co-product from the refining of oil producing plants or liquid hydrocarbons, said product or co-product comprising:
at least 20% by weight of an element selected from fats, triglycerides, glycerol, fatty acids, derivatives thereof and mixtures thereof; or
at least 20% by weight of an element selected from alkanes, alkenes, polyenes, and mixtures thereof, said alkanes, alkenes and polyenes comprising from 6 to 24 carbon atoms, in particular from 10 to 22 carbon atoms;
and optionally of a carbon-containing co-substrate,
contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation:
of a substrate constituted by or comprising a product or co-product from the refining of oil producing plants or liquid hydrocarbons, said product or co-product comprising:
at least 20% by weight of an element selected from fats, triglycerides, glycerol, fatty acids, derivatives thereof and mixtures thereof; or
at least 20% by weight of an element selected from alkanes, alkenes, polyenes, and mixtures thereof, said alkanes, alkenes and polyenes comprising from 6 to 24 carbon atoms, in particular from 10 to 22 carbon atoms;
and optionally of a carbon-containing co-substrate,
contained in the culture medium of said aerobic hyperhalophilic strain.

The invention also relates to the use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation:
of a substrate constituted by or comprising a product or co-product from the refining of oil producing plants or liquid hydrocarbons, said product or co-product comprising:
at least 20% by weight of an element selected from fats, triglycerides, glycerol, fatty acids, derivatives thereof and mixtures thereof; or
at least 20% by weight of an element selected from alkanes, alkenes, polyenes, and mixtures thereof, said alkanes, alkenes and polyenes comprising from 6 to 24 carbon atoms, in particular from 10 to 22 carbon atoms, in the absence of a carbon-containing co-substrate,
contained in the culture medium of said aerobic hyperhalophilic strain.

By "fats" in particular is meant oils, fats, and lipids.

The inventors have demonstrated the existence of a novel aerobic hyperhalophilic strain of *Haloferax* which, even under normal culture conditions, i.e. without stress, and aerobic conditions, degrades substrates such as oil, triglycerides, fatty acids or derivatives thereof, glycerol, alkanes, alkenes, polyenes, and optionally carbon-containing co-substrates.

The inventors have also demonstrated the existence of a novel aerobic hyperhalophilic strain of *Haloferax* which, even under normal culture conditions, i.e. without stress, and aerobic conditions, degrades substrates such as oil, triglycerides, fatty acids or derivatives thereof, glycerol, alkanes, alkenes, polyenes, in the absence of a carbon-containing co-substrate.

The expression "in the absence of a carbon-containing co-substrate" means that the culture medium is exclusively hydrophobic.

By "hyperhalophilic strain" is meant a strain that requires high concentrations of salts, in particular NaCl, $MgCl_2$ and/or $CaCl_2$, in its culture medium in order to grow. In particular it is a strain that develops, in particular optimally, in a culture medium the salt concentration of which, in particular NaCl, is comprised from about 100 g/L to about 300 g/L, in particular from about 100 g/L to about 250 g/L.

When the salt is in fact a mixture of salts, the concentration is comprised from about 100 g/L to about 300 g/L, in particular from about 100 g/L to about 250 g/L corresponds to the total concentration of salts in said mixture.

Said culture medium in particular comprises NaCl, and optionally further comprises $MgCl_2$ and/or $CaCl_2$ at concentrations from about 2 g/L to about 20 g/L.

By "degradation" is meant the transformation of said substrate and optionally of said carbon-containing co-substrate, by said strain, into one or more compounds of interest.

The compounds of interest are in particular biopolymers of the polyhydroxyalkanoate (PHA) type, bacteriorhodopsin and halostable esterases.

By "by-products of the triglycerides" in particular is meant glycerol, fatty acids, derivatives of fatty acids, in particular the methyl and ethyl esters of said fatty acids, or the co-products from oil refineries.

The co-products from oil refineries are in particular compositions comprising glycerol, fatty acids, derivatives of fatty acids, in particular the methyl and ethyl esters of said fatty acids, or mixtures thereof.

In particular, the substrates comprising triglycerides are in particular vegetable or animal oils and derivatives thereof, in particular frying oils.

The substrate is in particular selected from the group constituted by:
vegetable or animal oils, in particular vegetable oils, more particularly rapeseed oil, sunflower oil, maize oil, linseed oil, olive oil, castor oil, soya oil, palm oil, palm kernel oil, coconut oil, cottonseed oil, peanut oil, mixtures thereof, and derivatives thereof, in particular frying oils;
linear, branched or cyclic alkanes, comprising from 6 to 24 carbon atoms, in particular from 10 to 22 carbon atoms;
linear, branched or cyclic alkenes, comprising from 6 to 24 carbon atoms, in particular from 10 to 22 carbon atoms;
linear, branched or cyclic polyenes, comprising from 6 to 24 carbon atoms, in particular from 10 to 22 carbon atoms;
fatty acids, in particular saturated and unsaturated fatty acids, more particularly monounsaturated, diunsaturated and polyunsaturated fatty acids, said fatty acids comprising a carboxylic acid and a chain comprising from 6 to 24 carbon atoms, in particular from 10 to 22 carbon atoms, and derivatives thereof, in particular the esters of said fatty acids, more particularly the methyl and ethyl esters of said fatty acids;
triglycerides;
glycerol;
co-products from oil refineries, in particular vegetable oil, in particular neutralization pastes, deodorization condensates, gums, fatty acid distillates, fats from air flotation units and sludges from treatment plants.

By "polyene" is meant a compound comprising at least two carbon-carbon double bonds.

By "neutralization pastes" is meant the co-product in particular obtained by neutralization of said oils with soda.

By "deodorization condensates" in particular is meant the co-product obtained during scrubbing of the vapours obtained from the deodorization of said oils.

By "gums" in particular is meant the co-product obtained at the end of centrifugation of said oils during acid degumming.

By "fatty acid distillates" in particular is meant the co-product obtained during neutralizing distillation of said oils.

By "fats from air flotation units" in particular is meant the co-product obtained by treatment of the air flotation type of aqueous effluents from factories.

By "sludges from treatment plants" in particular is meant the by-product obtained by treatment of liquid effluents from factories.

By "carbon-containing co-substrate" is meant a compound comprising at least one carbon atom, said compound being degradable by said strain.

The carbon-containing substrate is in particular a sugar, in particular glucose.

By "culture medium of said hyperhalophilic strain" is meant a culture medium that is suitable for said hyperhalophilic strain, i.e. a culture medium containing the organic and mineral nutrients necessary for the growth of said hyperhalophilic strain. It is in particular a culture medium that comprises, besides said substrate and optionally the carbon-containing co-substrate, salts, in particular NaCl, at a concentration comprised from about 100 g/L to about 300 g/L, in particular from about 100 g/L to about 250 g/L, said culture medium optionally further comprising $MgCl_2$ and/or $CaCl_2$ at concentrations from about 2 g/L to about 20 g/L.

The culture medium may in particular comprise a source of nitrogen, for example a source of inorganic nitrogen, including ammonium sulphate, ammonium chloride or ammonium nitrate, or a source of organic nitrogen, in particular a yeast extract, peptone or a meat extract. In addition to the latter, said medium may further contain minerals, metal salts, and/or vitamins, if necessary.

According to an advantageous embodiment, the invention relates to a use as defined above, in which said substrate is said aerobic hyperhalophilic strain's only source of carbon and/or of energy in said culture medium.

According to an advantageous embodiment, the invention relates to a use as defined above, in which said substrate is said aerobic hyperhalophilic strain's main source of carbon and/or of energy in said culture medium.

By "main source of carbon and/or of energy" is meant a source of carbon and/or of energy corresponding to more than 50%, in particular more than 60%, 70%, 80% or 90%, by weight of the total of the sources of carbon and/or of energy of said aerobic hyperhalophilic strain.

When they are present in the culture medium, yeasts are a possible secondary source of carbon and/or of energy.

According to an advantageous embodiment, the invention relates to a use as defined above, of an aerobic hyperhalophilic strain the whole genome of which has a percentage identity of at least 90%, 91%, 92%, 93%, 94%, 95%, 96%, 97%, 98% or 99% with the whole genome of said strain S3S1.

According to an advantageous embodiment, the invention relates to a use as defined above, of an aerobic hyperhalophilic strain, being such that the percentage DNA-DNA hybridization between this aerobic hyperhalophilic strain and strain S3S1 is at least 90%, 91%, 92%, 93%, 94%, 95%, 96%, 97%, 98% or 99%.

According to another aspect, the invention relates to a method for the degradation of:
a substrate constituted by or comprising a product or co-product from the refining of oil producing plants or liquid hydrocarbons;

and optionally a carbon-containing co-substrate;
comprising a growth step for an aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in a culture medium comprising:
  a substrate constituted by or comprising an element selected from triglycerides, by-products thereof, alkanes, alkenes, polyenes and mixtures thereof;
  and optionally a carbon-containing co-substrate.

According to another aspect, the invention relates to a method for the degradation of:
  a substrate constituted by or comprising an element selected from triglycerides, by-products thereof, alkanes, alkenes, polyenes and mixtures thereof;
  and optionally a carbon-containing co-substrate;
comprising a growth step for an aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in a culture medium comprising:
  a substrate constituted by or comprising an element selected from triglycerides, by-products thereof, alkanes, alkenes, polyenes and mixtures thereof;
  and optionally a carbon-containing co-substrate.

According to another aspect, the invention relates to a method for the degradation of:
  a substrate constituted by or comprising a product or co-product from the refining of oil producing plants or liquid hydrocarbons;
  and optionally a carbon-containing co-substrate;
comprising a growth step for an aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium comprising:
  a substrate constituted by or comprising an element selected from triglycerides, by-products thereof, alkanes, alkenes, polyenes and mixtures thereof;
  and optionally a carbon-containing co-substrate.

According to another aspect, the invention relates to a method for the degradation of:
  a substrate constituted by or comprising an element selected from triglycerides, by-products thereof, alkanes, alkenes, polyenes and mixtures thereof;
  and optionally a carbon-containing co-substrate;
comprising a growth step for an aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium comprising:
  a substrate constituted by or comprising an element selected from triglycerides, by-products thereof, alkanes, alkenes, polyenes and mixtures thereof;
  and optionally a carbon-containing co-substrate.

According to another aspect, the invention relates to a method for the degradation of:
  a substrate constituted by or comprising a product or co-product from the refining of oil producing plants or liquid hydrocarbons, in the absence of a carbon-containing co-substrate;
comprising a growth step for an aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium comprising:
  a substrate constituted by or comprising an element selected from triglycerides, by-products thereof, alkanes, alkenes, polyenes and mixtures thereof, in the absence of a carbon-containing co-substrate.

According to another aspect, the invention relates to a method for the degradation of:
  a substrate constituted by or comprising an element selected from triglycerides, by-products thereof, alkanes, alkenes, polyenes and mixtures thereof, in the absence of a carbon-containing co-substrate;
comprising a growth step for an aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium comprising:
  a substrate constituted by or comprising an element selected from triglycerides, by-products thereof, alkanes, alkenes, polyenes and mixtures thereof, in the absence of a carbon-containing co-substrate.

By "growth step" is meant a step in which the biomass of said strain increases, and in which substrate and optionally carbon-containing co-substrate are consumed.

Thus, said growth step consists of bringing said aerobic hyperhalophilic strain S3S1 in its initial culture medium (i.e. a culture medium without said substrate and if applicable without said carbon-containing co-substrate) into contact with said substrate and optionally said carbon-containing co-substrate, forming the "culture medium of said hyperhalophilic strain" as defined above.

At the end of said growth step for said strain, substrate and optionally carbon-containing co-substrate are consumed and transformed into one or more compounds of interest.

According to an advantageous embodiment, the invention relates to a method as defined above, comprising a growth step for an aerobic hyperhalophilic strain the whole genome of which has a percentage identity of at least 90%, 91%, 92%, 93%, 94%, 95%, 96%, 97%, 98% or 99% with the whole genome of said strain S3S1.

According to an advantageous embodiment, the invention relates to a method as defined above, comprising a growth step for an aerobic hyperhalophilic strain, being such that the percentage DNA-DNA hybridization between this aerobic hyperhalophilic strain and strain S3S1 is at least 90%, 91%, 92%, 93%, 94%, 95%, 96%, 97%, 98% or 99%.

According to an advantageous embodiment, the invention relates to a method as defined above, in which the culture medium of said strain comprises a substrate, but not a carbon-containing co-substrate.

According to an advantageous embodiment, the invention relates to a method as defined above, in which the culture medium of said strain comprises a substrate selected from the group constituted by:
  vegetable and animal oils, in particular vegetable oils, more particularly rapeseed oil, sunflower oil, maize oil, linseed oil, olive oil, castor oil, soya oil, palm oil, palm kernel oil, coconut oil, cottonseed oil, peanut oil, mixtures thereof, and derivatives thereof, in particular frying oils;

linear, branched or cyclic alkanes, comprising from 6 to 24 carbon atoms, in particular from 10 to 22 carbon atoms;

linear, branched or cyclic alkenes, comprising from 6 to 24 carbon atoms, in particular from 10 to 22 carbon atoms;

linear, branched or cyclic polyenes, comprising from 6 to 24 carbon atoms, in particular from 10 to 22 carbon atoms;

fatty acids, in particular saturated and unsaturated fatty acids, more particularly monounsaturated, diunsaturated and polyunsaturated fatty acids, said fatty acids comprising a carboxylic acid and a chain comprising from 6 to 24 carbon atoms, in particular from 10 to 22 carbon atoms, and derivatives thereof, in particular the esters of said fatty acids, more particularly the methyl and ethyl esters of said fatty acids;

triglycerides;

glycerol;

co-products from oil refineries, in particular of vegetable oil, in particular neutralization pastes, deodorization condensates, gums, fatty acid distillates, fats from air flotation units and sludges from treatment plants, and mixtures thereof, contained in the culture medium of said aerobic hyperhalophilic strain.

According to an advantageous embodiment, the invention relates to a method as defined above, in which said substrate is:

a vegetable oil, in particular rapeseed oil, sunflower oil, maize oil, linseed oil, olive oil, castor oil, soya oil, palm oil, palm kernel oil, coconut oil, cottonseed oil, peanut oil, more particularly rapeseed oil or sunflower oil, a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, glycerol, or a mixture thereof.

According to an advantageous embodiment, the invention relates to a method as defined above, in which the culture medium of said strain comprises glycerol.

According to an advantageous embodiment, the invention relates to a method as defined above, in which the culture medium of said strain comprises a substrate and a carbon-containing co-substrate.

According to an advantageous embodiment, the invention relates to a method as defined above, in which the culture medium of said strain comprises glycerol and a carbon-containing co-substrate.

According to an advantageous embodiment, the invention relates to a method as defined above, in which the culture medium of said strain comprises a substrate and a carbon-containing co-substrate, said co-substrate being a sugar, in particular glucose.

According to an advantageous embodiment, the invention relates to a method as defined above, in which the culture medium of said strain comprises a substrate and glucose.

According to an advantageous embodiment, the invention relates to a method as defined above, in which the culture medium of said strain comprises a substrate and a carbon-containing co-substrate, said co-substrate being in particular a sugar, in particular glucose, the concentration of co-substrate being comprised from 1 g to 100 g/L, in particular from 1 g to 20 g/L, in particular from 1 g to 10 g/L, more particularly from 1 g to 5 g/L.

According to an advantageous embodiment, the invention relates to a method as defined above, in which the culture medium of said strain comprises a substrate in the absence of a carbon-containing co-substrate.

According to an advantageous embodiment, the invention relates to a method as defined above, in which the culture medium of said strain comprises:

a substrate selected from the group constituted by:

vegetable or animal oils, in particular vegetable oils, more particularly rapeseed oil, sunflower oil, maize oil, linseed oil, olive oil, castor oil, soya oil, palm oil, palm kernel oil, coconut oil, cottonseed oil, peanut oil, mixtures thereof, and derivatives thereof, in particular frying oils;

linear, branched or cyclic alkanes, comprising from 6 to 24 carbon atoms, in particular from 10 to 22 carbon atoms;

linear, branched or cyclic alkenes, comprising from 6 to 24 carbon atoms, in particular from 10 to 22 carbon atoms;

linear, branched or cyclic polyenes, comprising from 6 to 24 carbon atoms, in particular from 10 to 22 carbon atoms;

fatty acids, in particular saturated and unsaturated fatty acids, more particularly monounsaturated, diunsaturated and polyunsaturated fatty acids, said fatty acids comprising a carboxylic acid and a chain comprising from 6 to 24 carbon atoms, in particular from 10 to 22 carbon atoms, and derivatives thereof, in particular the esters of said fatty acids, more particularly the methyl and ethyl esters of said fatty acids;

triglycerides;

glycerol;

co-products from oil refineries, in particular of vegetable oil, in particular neutralization pastes, deodorization condensates, gums, fatty acid distillates, fats from air flotation units and sludges from treatment plants, and mixtures thereof, carbon-containing co-substrate, said co-substrate being a sugar, in particular glucose, contained in the culture medium of said aerobic hyperhalophilic strain.

According to an advantageous embodiment, the invention relates to a method as defined above, in which the culture medium of said strain comprises:

a substrate, said substrate being:
  a vegetable oil, in particular rapeseed oil, sunflower oil, maize oil, linseed oil, olive oil, castor oil, soya oil, palm oil, palm kernel oil, coconut oil, cottonseed oil, peanut oil, more particularly rapeseed oil or sunflower oil,
  a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
  a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
  glycerol,
  or a mixture thereof,
a carbon-containing co-substrate, said co-substrate being a sugar, in particular glucose, contained in the culture medium of said aerobic hyperhalophilic strain.

According to an advantageous embodiment, the invention relates to a method as defined above, in which the culture medium of said strain comprises glycerol, and a carbon-containing co-substrate, said co-substrate being a sugar, in particular glucose.

According to an advantageous embodiment, the invention relates to a method as defined above, in which the culture medium of said strain comprises a substrate and optionally a carbon-containing co-substrate selected from glycerol and stearate, glycerol and methyl stearate, glycerol and oleic acid, glycerol and methyl oleate, glycerol and erucic acid, glycerol and methyl erucate, glycerol and lauric acid, glycerol and methyl laurate, glycerol and oil, glycerol and rapeseed oil, glycerol and sunflower oil, glucose and stearate, glucose and methyl stearate, glucose and oleic acid, glucose and methyl oleate, glucose and erucic acid, glucose and methyl erucate, glucose and lauric acid, glucose and methyl laurate, glucose and oil, glucose and rapeseed oil, or glucose and sunflower oil.

According to an advantageous embodiment, the invention relates to a method as defined above, in which the culture medium comprises at least one salt.

By "salt" in particular is meant a salt with which said hyperhalophilic strain is compatible or which it needs.

According to an advantageous embodiment, the invention relates to a method as defined above, in which the salt is selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which said salt is present in the culture medium at a concentration comprised from about 100 g/L to about 300 g/L, in particular from about 100 g/L to about 250 g/L.

When the salt is in fact a mixture of salts, the concentration is comprised from about 100 g/L to about 300 g/L, in particular from about 100 g/L to about 250 g/L corresponds to the total concentration of said mixture of salts.

In particular, said hyperhalophilic strain develops optimally in a culture medium comprising from about 100 g/L to about 250 g/L of salt(s).

Such a concentration of salt(s) makes it possible to avoid any contamination of the external environment in the absence of sterilization of the culture medium.

According to an advantageous embodiment, the invention relates to a method as defined above, in which the culture medium of said strain comprises:
  a substrate selected from:
    rapeseed oil, sunflower oil, maize oil, linseed oil, olive oil, castor oil, soya oil, palm oil, palm kernel oil, coconut oil, cottonseed oil, peanut oil, in particular rapeseed oil or sunflower oil,
    glycerol,
    a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
    a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
  and mixtures thereof,
  and
  a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which the culture medium of said strain comprises:
  glycerol,
  and
  a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which the culture medium of said strain comprises:
  a substrate selected from:
    rapeseed oil, sunflower oil, maize oil, linseed oil, olive oil, castor oil, soya oil, palm oil, palm kernel oil, coconut oil, cottonseed oil, peanut oil, in particular rapeseed oil or sunflower oil,
    a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, and mixtures thereof, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which the culture medium of said strain comprises:

rapeseed oil, as substrate, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being in particular a mixture comprising NaCl, KCl, $CaCl_2.2H_2O$ and $MgCl_2.6H_2O$.

According to an advantageous embodiment, the invention relates to a method as defined above, in which the culture medium of said strain comprises:

oleic acid, as substrate, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being in particular a mixture comprising NaCl, KCl, $CaCl_2.2H_2O$ and $MgCl_2.6H_2O$.

According to an advantageous embodiment, the invention relates to a method as defined above, in which the culture medium of said strain comprises:

glycerol, as substrate, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being in particular a mixture comprising NaCl, KCl, $CaCl_2.2H_2O$ and $MgCl_2.6H_2O$.

According to an advantageous embodiment, the invention relates to a method as defined above, in which the culture medium of said strain comprises:

a substrate selected from:
rapeseed oil, sunflower oil, maize oil, linseed oil, olive oil, castor oil, soya oil, palm oil, palm kernel oil, coconut oil, cottonseed oil, peanut oil, in particular rapeseed oil or sunflower oil, a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, glycerol, and mixtures thereof, a carbon-containing co-substrate, in particular a sugar, in particular glucose, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which the culture medium of said strain comprises:

glycerol, as substrate, a carbon-containing co-substrate, in particular a sugar, in particular glucose, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which the culture medium of said strain comprises:

rapeseed oil, as substrate, glucose, as co-substrate, and salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being in particular a mixture comprising NaCl, KCl, $CaCl_2.2H_2O$ and $MgCl_2.6H_2O$.

According to an advantageous embodiment, the invention relates to a method as defined above, in which the culture medium of said strain comprises:

oleic acid, as substrate, glucose, as co-substrate, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being in particular a mixture comprising NaCl, KCl, $CaCl_2.2H_2O$ and $MgCl_2.6H_2O$.

According to an advantageous embodiment, the invention relates to a method as defined above, in which the culture medium of said strain comprises:

glycerol, as substrate, glucose, as co-substrate, and a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being in particular a mixture comprising NaCl, KCl, $CaCl_2.2H_2O$ and $MgCl_2.6H_2O$.

According to an advantageous embodiment, the invention relates to a method as defined above, in which the culture medium of said strain comprises:
a substrate selected from:
rapeseed oil, sunflower oil, maize oil, linseed oil, olive oil, castor oil, soya oil, palm oil, palm kernel oil, coconut oil, cottonseed oil, peanut oil, in particular rapeseed oil or sunflower oil,
glycerol,
a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid, and mixtures thereof,
said substrate being present in the culture medium at a concentration comprised from 1 to 100 g/l,
and
a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof,
said salt being present in the culture medium at a concentration comprised from about 100 g/L to about 300 g/L, in particular from about 100 g/L to about 250 g/L.

According to an advantageous embodiment, the invention relates to a method as defined above, in which the culture medium of said strain comprises:
glycerol,
said glycerol being present in the culture medium at a concentration comprised from 1 to 100 g/l,
and
a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof,
said salt being present in the culture medium at a concentration comprised from about 100 g/L to about 300 g/L, in particular from about 100 g/L to about 250 g/L.

According to an advantageous embodiment, the invention relates to a method as defined above, in which the culture medium of said strain comprises:
a substrate selected from:
rapeseed oil, sunflower oil, maize oil, linseed oil, olive oil, castor oil, soya oil, palm oil, palm kernel oil, coconut oil, cottonseed oil, peanut oil, in particular rapeseed oil or sunflower oil,
a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
glycerol,
and mixtures thereof,
said substrate being present in the culture medium at a concentration comprised from 1 to 100 g/l,
a carbon-containing co-substrate, said co-substrate being in particular a sugar, in particular glucose, the concentration of co-substrate being comprised from 1 g to 100 g/L, in particular from 1 g to 20 g/L, in particular from 1 g to 10 g/L, more particularly from 1 g to 5 g/L,
and
a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof,
said salt being present in the culture medium at a concentration comprised from about 100 g/L to about 300 g/L, in particular from about 100 g/L to about 250 g/L.

According to an advantageous embodiment, the invention relates to a method as defined above, in which the culture medium of said strain comprises:
glycerol,
said glycerol being present in the culture medium at a concentration comprised from 1 to 100 g/l,
a carbon-containing co-substrate, said co-substrate being in particular a sugar, in particular glucose, the concentration of co-substrate being comprised from 1 g to 100 g/L, in particular from 1 g to 20 g/L, in particular from 1 g to 10 g/L, more particularly from 1 g to 5 g/L,
and
a salt selected from NaCl, KCl, $CaCl_2$, $MgCl_2$, $MgSO_4$, hydrates thereof, in particular $CaCl_2.2H_2O$ and $MgCl_2.6H_2O$, and mixtures thereof,
said salt being present in the culture medium at a concentration comprised from about 100 g/L to about 300 g/L, in particular from about 100 g/L to about 250 g/L.

According to an advantageous embodiment, the invention relates to a method as defined above, in which the culture medium of said strain comprises:
rapeseed oil, oleic acid or glycerol, at a concentration comprised from 1 to 100 g/l,
NaCl, at a concentration comprised from about 100 g/L to about 300 g/L, in particular from about 100 g/L to about 250 g/L,
KCl, at a concentration comprised from 0 to 20 g/L, in particular from 2 g/L to 20 g/L,
$CaCl_2.2H_2O$, at a concentration comprised from 0 to 20 g/L, in particular from 2 g/L to 20 g/L,
$MgCl_2.6H_2O$, at a concentration comprised from 0 to 20 g/L, in particular from 2 g/L to 20 g/L.

According to an advantageous embodiment, the invention relates to a method as defined above, in which the culture medium of said strain comprises:

rapeseed oil, oleic acid or glycerol, at a concentration comprised from 1 to 100 g/l,
glucose, at a concentration comprised from 1 g to 100 g/L, in particular from 1 g to 20 g/L, in particular from 1 g to 10 g/L, more particularly from 1 g to 5 g/L,
NaCl, at a concentration comprised from about 100 g/L to about 300 g/L, in particular from about 100 g/L to about 250 g/L,
KCl, at a concentration comprised from 0 to 20 g/L, in particular from 2 g/L to 20 g/L,
$CaCl_2.2H_2O$, at a concentration comprised from 0 to 20 g/L, in particular from 2 g/L to 20 g/L,
$MgCl_2.6H_2O$, at a concentration comprised from 0 to 20 g/L, in particular from 2 g/L to 20 g/L.

According to an advantageous embodiment, the invention relates to a method as defined above, in which said strain is cultured in a medium in which the $NaCl/MgCl_2$ weight ratio is comprised from 15 to 100.

According to an advantageous embodiment, the invention relates to a method as defined above, in which said strain is cultured in a medium in which the $NaCl/CaCl_2$ weight ratio is comprised from 20 to 100.

When the $NaCl/MgCl_2$ weight ratio in the culture medium is comprised from 15 to 100, and/or the $NaCl/CaCl_2$ weight ratio is comprised from 20 to 100, the growth of the strain is improved relative to that of the same strain in a medium in which the $NaCl/MgCl_2$ weight ratio is not comprised from 15 to 100, and/or in which the $NaCl/CaCl_2$ weight ratio is not comprised from 20 to 100, in particular a medium not comprising $MgCl_2$ and/or $CaCl_2$.

According to an advantageous embodiment, the invention relates to a method as defined above, in which said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen.

According to an advantageous embodiment, the invention relates to a method as defined above, in which the ratio of carbon to nitrogen in the culture medium is comprised from 1 to 300.

When the ratio of carbon to nitrogen in the culture medium is comprised from 1 to 300, said strain may be under conditions of stress, and the quantity of substrate degraded may then be increased.

According to an advantageous embodiment, the invention relates to a method as defined above, in which the ratio of carbon to phosphorus in the culture medium is comprised from 80 to 800.

When the ratio of carbon to phosphorus in the culture medium is comprised from 80 to 800, said strain may be under conditions of stress, and the quantity of substrate degraded may then be increased.

According to an advantageous embodiment, the invention relates to a method as defined above, in which said strain is cultured in a medium in which:
the $NaCl/MgCl_2$ weight ratio is comprised from 15 to 100, and/or
the $NaCl/CaCl_2$ weight ratio is comprised from 20 to 100.

According to an advantageous embodiment, the invention relates to a method as defined above, in which:
said strain is cultured in a medium in which the $NaCl/MgCl_2$ weight ratio is comprised from 15 to 100, and/or the $NaCl/CaCl_2$ weight ratio is comprised from 20 to 100,
said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen,
the ratio of carbon to nitrogen in the culture medium is comprised from 1 to 300,
the ratio of carbon to phosphorus in the culture medium is comprised from 80 to 800.

According to an advantageous embodiment, the invention relates to a method as defined above, in which the culture medium of said strain comprises:
rapeseed oil, oleic acid or glycerol, at a concentration comprised from 1 to 100 g/l,
optionally glucose, at a concentration comprised from 1 g to 100 g/L, in particular from 1 g to 20 g/L, in particular from 1 g to 10 g/L, more particularly from 1 g to 5 g/L,
NaCl, at a concentration comprised from about 100 g/L to about 300 g/L, in particular from about 100 g/L to about 250 g/L,
KCl, at a concentration comprised from 0 to 20 g/L, in particular from 2 g/L to 20 g/L,
$CaCl_2.2H_2O$, at a concentration comprised from 0 to 20 g/L, in particular from 2 g/L to 20 g/L,
$MgCl_2.6H_2O$, at a concentration comprised from 0 to 20 g/L, in particular from 2 g/L to 20 g/L,
the $NaCl/MgCl_2$ weight ratio being comprised from 15 to 100, and/or the $NaCl/CaCl_2$ weight ratio being comprised from 20 to 100.

According to an advantageous embodiment, the invention relates to a method as defined above, in which:
said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen,
the ratio of carbon to nitrogen in the culture medium is comprised from 1 to 300,
the ratio of carbon to phosphorus in the culture medium is comprised from 80 to 800,
the culture medium of said strain comprises:
rapeseed oil, oleic acid or glycerol, at a concentration comprised from 1 to 100 g/l,
optionally glucose, at a concentration comprised from 1 g to 100 g/L, in particular from 1 g to 20 g/L, in particular from 1 g to 10 g/L, more particularly from 1 g to 5 g/L,
NaCl, at a concentration comprised from about 100 g/L to about 300 g/L, in particular from about 100 g/L to about 250 g/L,
KCl, at a concentration comprised from 0 to 20 g/L, in particular from 2 g/L to 20 g/L,
$CaCl_2.2H_2O$, at a concentration comprised from 0 to 20 g/L, in particular from 2 g/L to 20 g/L,
$MgCl_2.6H_2O$, at a concentration comprised from 0 to 20 g/L, in particular from 2 g/L to 20 g/L,
the $NaCl/MgCl_2$ weight ratio being comprised from 15 to 100, and/or the $NaCl/CaCl_2$ weight ratio being comprised from 20 to 100.

According to an advantageous embodiment, the invention relates to a method as defined above, in which the growth step for said strain is carried out at a temperature comprised from 20 to 50° C., in particular about 37° C.

According to an advantageous embodiment, the invention relates to a method as defined above, in which the pH of the culture medium is comprised from about pH 5 to about pH 9, more particularly from about pH 6 to about pH 8, the pH of the culture medium being even more advantageously equal to about pH 7.

According to an advantageous embodiment, the invention relates to a method as defined above, carried out under non-sterile conditions.

According to an advantageous embodiment, the invention relates to a method as defined above, carried out under non-sterile conditions, in which the culture medium comprises at least one salt, in particular selected from NaCl, KCl, $CaCl_2$, $MgCl_2$, $MgSO_4$, hydrates thereof, in particular $CaCl_2 \cdot 2H_2O$ and $MgCl_2 \cdot 6H_2O$, and mixtures thereof, said salt being present in the culture medium at a concentration comprised from about 100 g/L to about 300 g/L, in particular from about 100 g/L to about 250 g/L.

According to an advantageous embodiment, the invention relates to a use as defined above, in which said method for the degradation:
of a substrate constituted by or comprising a product or co-product from the refining of oil producing plants or liquid hydrocarbons,
and optionally of a carbon-containing co-substrate, is implemented for preparing a biopolymer of the polyhydroxyalkanoate (PHA) type.

According to an advantageous embodiment, the invention relates to a use as defined above, in which said method for the degradation:
of a substrate constituted by or comprising an element selected from triglycerides, by-products thereof, alkanes, alkenes, polyenes and mixtures thereof;
and optionally of a carbon-containing co-substrate, is implemented for preparing a biopolymer of the polyhydroxyalkanoate (PHA) type.

By "polyhydroxyalkanoate" in particular is meant a polymer the repeat unit or units of which, independently of one another, are of the following formula (I):

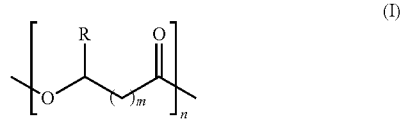

in which:
m is equal to 0, 1, 2, 3 or 4;
n is in particular comprised from 1000 to 20000;
R represents H or a group comprising from 1 to 20 carbon atoms, in particular an alkyl chain, more particularly a linear alkyl chain.

According to an advantageous embodiment, the present invention relates to a use as defined above, in which said biopolymer of the polyhydroxyalkanoate type does not comprise a C≡C bond.

According to an advantageous embodiment, the present invention relates to a use as defined above, in which said biopolymer of the polyhydroxyalkanoate type has short side chains.

By "short side chains" is meant the methyl and ethyl chains.

By "polyhydroxyalkanoate with short side chains" in particular is meant the polymers the repeat unit or units of which, independently of one another, are of formula (I) as defined above, in which R is a methyl or an ethyl.

According to an advantageous embodiment, the present invention relates to a use as defined above, in which said biopolymer is of the poly(3-hydroxybutyrate), poly(3-hydroxyvalerate), or poly(3-hydroxybutyrate-co-3-hydroxyvalerate) type.

Poly(3-hydroxybutyrate) corresponds to a polymer the repeat unit of which is of formula (I) as described above, in which m is equal to 1 and R represents a methyl.

Poly(3-hydroxyvalerate) corresponds to a polymer the repeat unit of which is of formula (I) as described above, in which m is equal to 1 and R represents an ethyl.

Poly(3-hydroxybutyrate-co-3-hydroxyvalerate) corresponds to a copolymer comprising two repeat units of formula (I) as described above, for which m is equal to 1 and R represents a methyl and an ethyl respectively.

According to an advantageous embodiment, the present invention relates to a use as defined above, in which said biopolymer of the poly(3-hydroxybutyrate-co-3-hydroxyvalerate) type with a hydroxybutyrate/hydroxyvalerate molar composition equal to about 96/4.

According to another aspect, the present invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, said culture being obtained after growth in a medium comprising:
a substrate constituted by or comprising a product or co-product from the refining of oil producing plants or liquid hydrocarbons,
and optionally a carbon-containing co-substrate.

According to another aspect, the present invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, said culture being obtained after growth in a medium comprising:
a substrate constituted by or comprising a product or co-product from the refining of oil producing plants or liquid hydrocarbons,
and optionally a carbon-containing co-substrate.

According to another aspect, the present invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, said culture being obtained after growth in a medium comprising:
a substrate constituted by or comprising a product or co-product from the refining of oil producing plants or liquid hydrocarbons, in the absence of a carbon-containing co-substrate.

According to another aspect, the present invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, said culture being obtained after growth in a medium comprising:
- a substrate constituted by or comprising an element selected from triglycerides, by-products thereof, alkanes, alkenes, polyenes and mixtures thereof;
- and optionally a carbon-containing co-substrate.

According to another aspect, the present invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, said culture being obtained after growth in a medium comprising:
- a substrate constituted by or comprising an element selected from triglycerides, by-products thereof, alkanes, alkenes, polyenes and mixtures thereof;
- and optionally a carbon-containing co-substrate.

According to another aspect, the present invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, said culture being obtained after growth in a medium comprising:
- a substrate constituted by or comprising an element selected from triglycerides, by-products thereof, alkanes, alkenes, polyenes and mixtures thereof, in the absence of a carbon-containing co-substrate.

By "lysis" is meant disintegration of the membrane of the cells of said strain by a physical, chemical or biological agent.

According to an advantageous embodiment, the present invention relates to a method as defined above, in which said biopolymer of the polyhydroxyalkanoate type does not comprise a C≡C bond.

According to an advantageous embodiment, the present invention relates to a method as defined above, in which said biopolymer of the polyhydroxyalkanoate type has short side chains.

According to an advantageous embodiment, the present invention relates to a method as defined above, in which said biopolymer is of the poly(3-hydroxybutyrate), poly(3-hydroxyvalerate), or poly(3-hydroxybutyrate-co-3-hydroxyvalerate) type.

According to an advantageous embodiment, the present invention relates to a method as defined above, in which said biopolymer of the poly(3-hydroxybutyrate-co-3-hydroxyvalerate) type has a hydroxybutyrate/hydroxyvalerate molar composition equal to about 96/4.

According to an advantageous embodiment, the invention relates to a method as defined above, comprising a step of lysis of a culture of an aerobic hyperhalophilic strain the whole genome of which has a percentage identity of at least 90%, 91%, 92%, 93%, 94%, 95%, 96%, 97%, 98% or 99% with the whole genome of said strain S3S1.

According to an advantageous embodiment, the invention relates to a method as defined above, comprising a step of lysis of a culture of an aerobic hyperhalophilic strain, being such that the percentage DNA-DNA hybridization between this aerobic hyperhalophilic strain and strain S3S1 is at least 90%, 91%, 92%, 93%, 94%, 95%, 96%, 97%, 98% or 99%.

According to an advantageous embodiment, the invention relates to a method as defined above, in which the lysis step (a) comprises bringing said culture of said strain, optionally in the lyophilized form, into contact with a detergent in order to obtain a cellular lysate.

According to another advantageous embodiment, the invention relates to a method as defined above, in which the lysis step (a) comprises sonication of said culture of said strain in order to obtain a cellular lysate.

According to another advantageous embodiment, the invention relates to a method as defined above, in which the lysis step (a) comprises bringing said culture of said strain, optionally in the lyophilized form, into contact with a detergent, then sonication of the mixture thus obtained, in order to obtain a cellular lysate.

In particular, said PHA is present in the cytoplasm of the cells of said strain.

Said detergent is for example an anionic surfactant, in particular a salt of sodium, of potassium, of ammonium or of alkyl ammonium of sulphates, more particularly those obtained by sulphation of alcohols comprising an alkyl chain with 8 to 18 carbon atoms.

Specific examples of alkyl sulphates useful in the present invention comprise sodium dodecyl sulphate, potassium dodecyl sulphate, ammonium dodecyl sulphate, monoethanolammonium dodecyl sulphate, diethanolammonium dodecyl sulphate, triethanolammonium dodecyl sulphate, tetraethanolammonium dodecyl sulphate, and sodium lauryl ether sulphate.

Sonication is carried out for example at a power of 8.1 W, for 3 times 2 minutes, in particular using Vibra-cell Bioblock Scientific 72442 apparatus.

According to an advantageous embodiment, the invention relates to a method as defined above, in which the lysis step (a) is carried out at a temperature comprised from about 0° C. to about 12° C., in particular at a temperature of about 4° C.

According to an advantageous embodiment, the invention relates to a method as defined above comprising a step (b) of extraction of the PHA from the cellular lysate.

According to an advantageous embodiment, the invention relates to a method as defined above, in which step (b) of extraction of PHA is carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume, in order to obtain said biopolymer of the PHA type and a cellular fraction.

According to an advantageous embodiment, the invention relates to a method as defined above comprising (c) a step of purification of the PHA.

According to a particularly advantageous embodiment, the invention relates to a method as defined above, in which said step of purification of the PHA is carried out by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction.

According to a particularly advantageous embodiment, the invention relates to a method as defined above, in which said step of purification of the PHA is carried out by washing said biopolymer of the PHA type and said cellular fraction with an organic solvent or a mixture of organic solvents, for example a mixture of acetone and ethanol, then adding an organic solvent, in particular chloroform, in particular at a temperature comprised from 20° C. to 80° C., more particularly at a temperature from 45° C. to 65° C., in order to obtain a solution of PHA in said organic solvent, said solution being devoid of the cellular fraction.

According to an advantageous embodiment, the invention relates to a method as defined above comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in order to obtain a cellular lysate,
a step (b) of extraction of the PHA from the cellular lysate,
(c) a step of purification of the PHA.

According to an advantageous embodiment, the invention relates to a method as defined above comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in order to obtain a cellular lysate,
a step (b) of extraction of the PHA from the cellular lysate,
(c) a step of purification of the PHA.

According to an advantageous embodiment, the invention relates to a method as defined above comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in order to obtain a cellular lysate,
said lysis step (a) comprising:
bringing said culture of said strain, optionally in the lyophilized form, into contact with a detergent in order to obtain a cellular lysate,
sonication of said culture of said strain in order to obtain a cellular lysate, or
bringing said culture of said strain, optionally in the lyophilized form, into contact with a detergent, then sonication of the mixture thus obtained, in order to obtain a cellular lysate,
a step (b) of extraction of the PHA from the cellular lysate,
said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume,
in order to obtain said biopolymer of the PHA type and a cellular fraction,
(c) a step of purification of the PHA,
said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in order to obtain a cellular lysate,
said lysis step (a) comprising:
bringing said culture of said strain, optionally in the lyophilized form, into contact with a detergent in order to obtain a cellular lysate,
sonication of said culture of said strain in order to obtain a cellular lysate, or
bringing said culture of said strain, optionally in the lyophilized form, into contact with a detergent, then sonication of the mixture thus obtained, in order to obtain a cellular lysate,
a step (b) of extraction of the PHA from the cellular lysate,
said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume,
in order to obtain said biopolymer of the PHA type and a cellular fraction,
(c) a step of purification of the PHA,
said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction.

According to an advantageous embodiment, the invention relates to a method as defined above, in which said strain is cultured on a medium comprising a substrate selected from the group constituted by:
vegetable and animal oils, in particular vegetable oils, more particularly rapeseed oil, sunflower oil, maize oil, linseed oil, olive oil, castor oil, soya oil, palm oil, palm kernel oil, coconut oil, cottonseed oil, peanut oil, and derivatives thereof, in particular frying oils;
linear, branched or cyclic alkanes, comprising from 6 to 24 carbon atoms, in particular from 10 to 22 carbon atoms;
linear, branched or cyclic alkenes, comprising from 6 to 24 carbon atoms, in particular from 10 to 22 carbon atoms;
linear, branched or cyclic polyenes, comprising from 6 to 24 carbon atoms, in particular from 10 to 22 carbon atoms;
fatty acids, in particular saturated and unsaturated fatty acids, more particularly monounsaturated, diunsaturated and polyunsaturated fatty acids, said fatty acids comprising a carboxylic acid and a chain comprising from 6 to 24 carbon atoms, in particular from 10 to 22 carbon atoms, and derivatives thereof, in particular the esters of said fatty acids, more particularly the methyl and ethyl esters of said fatty acids;
triglycerides;
glycerol;
co-products from oil refineries, in particular of vegetable oil, in particular neutralization pastes, deodorization condensates, gums, fatty acid distillates, fats from air flotation units and sludges from treatment plants.

According to an advantageous embodiment, the invention relates to a method as defined above, in which said substrate is:
- a vegetable oil, in particular rapeseed oil, sunflower oil, maize oil, linseed oil, olive oil, castor oil, soya oil, palm oil, palm kernel oil, coconut oil, cottonseed oil, peanut oil, more particularly rapeseed oil or sunflower oil,
- a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
- a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
- glycerol, or a mixture thereof.

According to an advantageous embodiment, the invention relates to a method as defined above, in which said strain is cultured on a medium comprising a substrate and a carbon-containing co-substrate.

According to an advantageous embodiment, the invention relates to a method as defined above, in which said strain is cultured on a medium comprising a substrate and a carbon-containing co-substrate, said co-substrate being a sugar, in particular glucose.

According to an advantageous embodiment, the invention relates to a method as defined above, in which said strain is cultured on a medium comprising a substrate and a carbon-containing co-substrate, said co-substrate being in particular a sugar, in particular glucose, the concentration of co-substrate being comprised from 1 g to 100 g/L, in particular from 1 g to 20 g/L, in particular from 1 g to 10 g/L, more particularly from 1 g to 5 g/L.

According to an advantageous embodiment, the invention relates to a method as defined above, in which said strain is cultured on a medium comprising:
- a substrate selected from the group constituted by:
  - vegetable or animal oils, in particular vegetable oils, more particularly rapeseed oil, sunflower oil, maize oil, linseed oil, olive oil, castor oil, soya oil, palm oil, palm kernel oil, coconut oil, cottonseed oil, peanut oil, and derivatives thereof, in particular frying oils;
  - linear, branched or cyclic alkanes, comprising from 6 to 24 carbon atoms, in particular from 10 to 22 carbon atoms;
  - linear, branched or cyclic alkenes, comprising from 6 to 24 carbon atoms, in particular from 10 to 22 carbon atoms;
  - linear, branched or cyclic polyenes, comprising from 6 to 24 carbon atoms, in particular from 10 to 22 carbon atoms;
  - fatty acids, in particular saturated and unsaturated fatty acids, more particularly monounsaturated, diunsaturated and polyunsaturated fatty acids, said fatty acids comprising a carboxylic acid and a chain comprising from 6 to 24 carbon atoms, in particular from 10 to 22 carbon atoms, and derivatives thereof, in particular the esters of said fatty acids, more particularly the methyl and ethyl esters of said fatty acids;
  - triglycerides;
  - glycerol;
  - co-products from oil refineries, in particular of vegetable oil, in particular neutralization pastes, deodorization condensates, gums, fatty acid distillates, fats from air flotation units and sludges from treatment plants, and mixtures thereof,
- a carbon-containing co-substrate, said co-substrate being a sugar, in particular glucose, contained in the culture medium of said aerobic hyperhalophilic strain.

According to an advantageous embodiment, the invention relates to a method as defined above, in which said strain is cultured on a medium comprising:
- a substrate, said substrate being:
  - a vegetable oil, in particular rapeseed oil, sunflower oil, maize oil, linseed oil, olive oil, castor oil, soya oil, palm oil, palm kernel oil, coconut oil, cottonseed oil, peanut oil, more particularly rapeseed oil or sunflower oil,
  - a saturated or unsaturated fatty acid selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
  - a triglyceride constituted by glycerol the three hydroxyl groups of which are esterified by fatty acids selected from caprylic, capric, lauric, myristic, palmitic, stearic, arachidic, behenic, lignoceric, cerotic, sapienic, elaidic, vaccenic, linoelaidic, α-linolenic, erucic, docosahexaenoic, oleic, linoleic, arachidonic, eicosapentaenoic, hexadecatrienoic, stearidonic, eicosatrienoic, heneicosapentaenoic, docosapentaenoic, tetracosapentaenoic, tetracosahexaenoic, gamma-linolenic, eicosadienoic, docosadienoic, adrenic, tetracosatetraenoic, eicosenoic, pinolenic, podocarpic and myristoleic acid,
  - glycerol,
  - or a mixture thereof,
- a carbon-containing co-substrate, said co-substrate being a sugar, in particular glucose, contained in the culture medium of said aerobic hyperhalophilic strain.

According to an advantageous embodiment, the invention relates to a method as defined above, in which said strain is cultured in a medium comprising a substrate and optionally a carbon-containing co-substrate selected from glycerol and stearate, glycerol and methyl stearate, glycerol and oleic acid, glycerol and methyl oleate, glycerol and erucic acid, glycerol and methyl erucate, glycerol and lauric acid, glycerol and methyl laurate, glycerol and oil, glycerol and rapeseed oil, glycerol and sunflower oil, glucose and stearate, glucose and methyl stearate, glucose and oleic acid, glucose and methyl oleate, glucose and erucic acid, glucose and methyl erucate, glucose and lauric acid, glucose and methyl laurate, glucose and oil, glucose and rapeseed oil, or glucose and sunflower oil.

According to an advantageous embodiment, the invention relates to a method as defined above, in which said strain is cultured in a medium comprising at least one salt.

According to an advantageous embodiment, the invention relates to a method as defined above, in which the salt is selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which said strain is cultured in a medium in which the $NaCl/MgCl_2$ weight ratio is comprised from 15 to 100.

According to an advantageous embodiment, the invention relates to a method as defined above, in which said strain is cultured in a medium in which the $NaCl/CaCl_2$ weight ratio is comprised from 20 to 100.

When the $NaCl/MgCl_2$ weight ratio in the culture medium is comprised from 15 to 100, and/or the $NaCl/CaCl_2$ weight ratio is comprised from 20 to 100, the growth of the strain is improved relative to that of the same strain in a medium in which the $NaCl/MgCl_2$ weight ratio is not comprised from 15 to 100, and/or in which the $NaCl/CaCl_2$ weight ratio is not comprised from 20 to 100, in particular a medium not comprising $MgCl_2$ and/or $CaCl_2$.

According to an advantageous embodiment, the invention relates to a method as defined above, in which said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen.

According to an advantageous embodiment, the invention relates to a method as defined above, in which the ratio of carbon to nitrogen in the culture medium is comprised from 1 to 300.

When the ratio of carbon to nitrogen in the culture medium is comprised from 1 to 300, said strain may be under conditions of stress, and the quantity of PHA produced may then be increased.

According to an advantageous embodiment, the invention relates to a method as defined above, in which the ratio of carbon to phosphorus in the culture medium is comprised from 80 to 800.

When the ratio of carbon to phosphorus in the culture medium is comprised from 80 to 800, said strain may be under conditions of stress, and the quantity of PHA produced may then be increased.

According to an advantageous embodiment, the invention relates to a method as defined above, carried out under non-sterile conditions.

According to an advantageous embodiment, the invention relates to a method as defined above, carried out under non-sterile conditions, in which the culture medium comprises at least one salt, in particular selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being present in the culture medium at a concentration comprised from about 100 g/L to about 300 g/L, in particular from about 100 g/L to about 250 g/L.

According to an advantageous embodiment, the invention relates to a method as defined above comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in a culture medium, in order to obtain a cellular lysate, said lysis step (a) comprising:
bringing said culture of said strain, optionally in the lyophilized form, into contact with a detergent in order to obtain a cellular lysate,
sonication of said culture of said strain in order to obtain a cellular lysate, or
bringing said culture of said strain, optionally in the lyophilized form, into contact with a detergent, then sonication of the mixture thus obtained, in order to obtain a cellular lysate,
said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume,
in order to obtain said biopolymer of the PHA type and a cellular fraction,
(c) a step of purification of the PHA,
said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction,
and in which the culture medium of said strain comprises:
rapeseed oil, oleic acid or glycerol, at a concentration comprised from 1 to 100 g/l,
optionally glucose, at a concentration comprised from 1 g to 100 g/L, in particular from 1 g to 20 g/L, in particular from 1 g to 10 g/L, more particularly from 1 g to 5 g/L,
NaCl, at a concentration comprised from about 100 g/L to about 300 g/L, in particular from about 100 g/L to about 250 g/L,
KCl, at a concentration comprised from 0 to 20 g/L, in particular from 2 g/L to 20 g/L,
$CaCl_2.2H_2O$, at a concentration comprised from 0 to 20 g/L, in particular from 2 g/L to 20 g/L,
$MgCl_2.6H_2O$, at a concentration comprised from 0 to 20 g/L, in particular from 2 g/L to 20 g/L,
the $NaCl/MgCl_2$ weight ratio being comprised from 15 to 100, and/or the $NaCl/CaCl_2$ weight ratio being comprised from 20 to 100.

According to an advantageous embodiment, the invention relates to a method as defined above comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium, in order to obtain a cellular lysate,
said lysis step (a) comprising:
bringing said culture of said strain, optionally in the lyophilized form, into contact with a detergent in order to obtain a cellular lysate,
sonication of said culture of said strain in order to obtain a cellular lysate, or
bringing said culture of said strain, optionally in the lyophilized form, into contact with a detergent, then sonication of the mixture thus obtained, in order to obtain a cellular lysate,
said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume, in order to obtain said biopolymer of the PHA type and a cellular fraction, (c) a step of purification of the PHA, said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction, and in which the culture medium of said strain comprises:
- rapeseed oil, oleic acid or glycerol, at a concentration comprised from 1 to 100 g/l,
- optionally glucose, at a concentration comprised from 1 g to 100 g/L, in particular from 1 g to 20 g/L, in particular from 1 g to 10 g/L, more particularly from 1 g to 5 g/L,
- NaCl, at a concentration comprised from about 100 g/L to about 300 g/L, in particular from about 100 g/L to about 250 g/L,
- KCl, at a concentration comprised from 0 to 20 g/L, in particular from 2 g/L to 20 g/L,
- $CaCl_2.2H_2O$, at a concentration comprised from 0 to 20 g/L, in particular from 2 g/L to 20 g/L,
- $MgCl_2.6H_2O$, at a concentration comprised from 0 to 20 g/L, in particular from 2 g/L to 20 g/L,
- the $NaCl/MgCl_2$ weight ratio being comprised from 15 to 100, and/or the $NaCl/CaCl_2$ weight ratio being comprised from 20 to 100.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in a culture medium, in order to obtain a cellular lysate, said lysis step (a) comprising:
- bringing said culture of said strain, optionally in the lyophilized form, into contact with a detergent in order to obtain a cellular lysate,
- sonication of said culture of said strain in order to obtain a cellular lysate, or
- bringing said culture of said strain, optionally in the lyophilized form, into contact with a detergent, then sonication of the mixture thus obtained, in order to obtain a cellular lysate, said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume, in order to obtain said biopolymer of the PHA type and a cellular fraction, (c) a step of purification of the PHA, said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction, and in which:
- said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen,
- the ratio of carbon to nitrogen in the culture medium is comprised from 1 to 300,
- the ratio of carbon to phosphorus in the culture medium is comprised from 80 to 800,
- the culture medium of said strain comprises:
  - rapeseed oil, oleic acid or glycerol, at a concentration comprised from 1 to 100 g/l,
  - optionally glucose, at a concentration comprised from 1 g to 100 g/L, in particular from 1 g to 20 g/L, in particular from 1 g to 10 g/L, more particularly from 1 g to 5 g/L,
  - NaCl, at a concentration comprised from about 100 g/L to about 300 g/L, in particular from about 100 g/L to about 250 g/L,
  - KCl, at a concentration comprised from 0 to 20 g/L, in particular from 2 g/L to 20 g/L,
  - $CaCl_2.2H_2O$, at a concentration comprised from 0 to 20 g/L, in particular from 2 g/L to 20 g/L,
  - $MgCl_2.6H_2O$, at a concentration comprised from 0 to 20 g/L, in particular from 2 g/L to 20 g/L,
  - the $NaCl/MgCl_2$ weight ratio being comprised from 15 to 100, and/or the $NaCl/CaCl_2$ weight ratio being comprised from 20 to 100.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium, in order to obtain a cellular lysate, said lysis step (a) comprising:
- bringing said culture of said strain, optionally in the lyophilized form, into contact with a detergent in order to obtain a cellular lysate,
- sonication of said culture of said strain in order to obtain a cellular lysate, or
- bringing said culture of said strain, optionally in the lyophilized form, into contact with a detergent, then sonication of the mixture thus obtained, in order to obtain a cellular lysate, said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume, in order to obtain said biopolymer of the PHA type and a cellular fraction, (c) a step of purification of the PHA, said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction, and in which:

said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen, the ratio of carbon to nitrogen in the culture medium is comprised from 1 to 300, the ratio of carbon to phosphorus in the culture medium is comprised from 80 to 800, the culture medium of said strain comprises:

rapeseed oil, oleic acid or glycerol, at a concentration comprised from 1 to 100 g/l, optionally glucose, at a concentration comprised from 1 g to 100 g/L, in particular from 1 g to 20 g/L, in particular from 1 g to 10 g/L, more particularly from 1 g to 5 g/L, NaCl, at a concentration comprised from about 100 g/L to about 300 g/L, in particular from about 100 g/L to about 250 g/L, KCl, at a concentration comprised from 0 to 20 g/L, in particular from 2 g/L to 20 g/L, $CaCl_2.2H_2O$, at a concentration comprised from 0 to 20 g/L, in particular from 2 g/L to 20 g/L, $MgCl_2.6H_2O$, at a concentration comprised from 0 to 20 g/L, in particular from 2 g/L to 20 g/L, the $NaCl/MgCl_2$ weight ratio being comprised from 15 to 100, and/or the $NaCl/CaCl_2$ weight ratio being comprised from 20 to 100.

According to another aspect, the present invention relates to a PHA that is obtainable by a method as defined above.

According to an advantageous embodiment, the present invention relates to a PHA having a polymolecularity index from 1.0 to 2.0, in particular from 1.5 to 1.9, more particularly from 1.6 to 1.8, in particular of about 1.7.

According to another aspect, the present invention relates to a PHA with a weight-average molecular weight above 500 000 g/mol, in particular above 500 000 g/mol, 600 000 g/mol, 700 000 g/mol, 800 000 g/mol, 900 000 g/mol, or 1 000 000 g/mol.

According to another aspect, the present invention relates to a PHA with a weight-average molecular weight above 500 000 g/mol, in particular above 500 000 g/mol, 600 000 g/mol, 700 000 g/mol, 800 000 g/mol, 900 000 g/mol, or 1 000 000 g/mol, characterized by short side chains.

According to another aspect, the present invention relates to a PHA with a weight-average molecular weight above 500 000 g/mol, in particular above 500 000 g/mol, 600 000 g/mol, 700 000 g/mol, 800 000 g/mol, 900 000 g/mol, or 1 000 000 g/mol, said PHA having a polymolecularity index from 1.0 to 2.0, in particular from 1.5 to 1.9, more particularly from 1.6 to 1.8, in particular of about 1.7.

According to another aspect, the present invention relates to a PHA with a weight-average molecular weight above 500 000 g/mol, in particular above 500 000 g/mol, 600 000 g/mol, 700 000 g/mol, 800 000 g/mol, 900 000 g/mol, or 1 000 000 g/mol, characterized by short side chains, said PHA having a polymolecularity index from 1.0 to 2.0, in particular from 1.5 to 1.9, more particularly from 1.6 to 1.8, in particular of about 1.7.

According to another aspect, the present invention relates to a PHA with a weight-average molecular weight above 500 000 g/mol, in particular above 500 000 g/mol, 600 000 g/mol, 700 000 g/mol, 800 000 g/mol, 900 000 g/mol, or 1 000 000 g/mol, characterized by short side chains and a given transparency index.

According to another aspect, the present invention relates to a PHA with a number-average molecular weight above 400 000 g/mol, in particular above 450 000 g/mol, 500 000 g/mol, 550 000 g/mol, or 600 000 g/mol.

According to another aspect, the present invention relates to a PHA with a number-average molecular weight above 400 000 g/mol, in particular above 450 000 g/mol, 500 000 g/mol, 550 000 g/mol, or 600 000 g/mol, characterized by short side chains.

According to another aspect, the present invention relates to a PHA with a number-average molecular weight above 400 000 g/mol, in particular above 450 000 g/mol, 500 000 g/mol, 550 000 g/mol, or 600 000 g/mol, said PHA having a polymolecularity index from 1.0 to 2.0, in particular from 1.5 to 1.9, more particularly from 1.6 to 1.8, in particular of about 1.7.

According to another aspect, the present invention relates to a PHA with a number-average molecular weight above 400 000 g/mol, in particular above 450 000 g/mol, 500 000 g/mol, 550 000 g/mol, or 600 000 g/mol, characterized by short side chains, said PHA having a polymolecularity index from 1.0 to 2.0, in particular from 1.5 to 1.9, more particularly from 1.6 to 1.8, in particular of about 1.7.

According to another aspect, the present invention relates to a PHA with a number-average molecular weight above 400 000 g/mol, in particular above 450 000 g/mol, 500 000 g/mol, 550 000 g/mol, or 600 000 g/mol, characterized by short side chains and a given transparency index.

By "short side chains" is meant the methyl and ethyl chains.

The weight-average molecular weight, the number-average molecular weight and the polymolecularity index of the PHA of the invention can be determined by gel permeation chromatography (GPC), in particular with a differential refractometer (RI) or light scattering (LS) as the method of detection.

The transparency of a solution of PHA can be determined by turbidity. Turbidity is an intrinsic property of materials, which is related to the attenuation of the intensity of light when it passes through materials.

The values of absorbance (Abs) can be determined using a Varian, Cary 60 spectrophotometer and the turbidity is then calculated as follows:

$$\text{Turbidity } T=1-10^{(-Abs)}.$$

According to an advantageous embodiment, the present invention relates to a PHA of the poly(3-hydroxybutyrate), poly(3-hydroxyvalerate), or poly(3-hydroxybutyrate-co-3-hydroxyvalerate) type.

According to an advantageous embodiment, the present invention relates to a PHA of the poly(3-hydroxybutyrate-co-3-hydroxyvalerate) type the hydroxybutyrate/hydroxyvalerate molar composition of which is equal to about 96/4.

According to an advantageous embodiment, the present invention relates to a PHA as defined above comprising or constituted by a biopolymer with a P(HB-co-HV) unit in the proportions 96/4, said polymer having a polydispersity index from 1.0 to 2.0, in particular from 1.5 to 1.9, more particularly from 1.6 to 1.8, in particular of about 1.7, a Tg comprised from −10° C. to +10° C., in particular from −5° C. to +10° C., in particular of about +5° C., a Tm greater than or equal to 140°, in particular comprised from 140° C. to 170° C., more particularly from 145° C. to 165° C., in particular about 157° C.

The glass transition temperature (Tg) and the melting point (Mp) can be determined by differential scanning calorimetry (DSC). The melting point can be determined at the 1st passage and the glass transition temperature at the 2nd passage.

In particular, the glass transition temperature (Tg) and the melting point (Mp) can be determined by DSC, on a Diamond DSC apparatus (Perkin Elmer): the melting point is for example determined at the first passage and the glass transition temperature at the second passage according to the following temperature programme: 1) from 20° C. to −50° C. at 40° C./min; 2) 3 min at −50° C.; 3) first passage: from −50° C. to 200° C. at 20° C./min; 4) from 180° C. to −50° C. at 200° C./min; 5) 3 min at −50° C.; 6) second passage: −50° C. to 200° C. at 20° C./min.

The solutions of PHA according to the invention, in a solvent, in particular organic, are perfectly clear, and very viscous.

The measurements of viscosity may be carried out either with a rheometer (TA Instrument, HR2) or with a falling ball viscosimeter, if the solution is more fluid (Lovis, Anton Paar). The rheological measurements may be carried out either by flow or by shearing, and can give the loss and storage moduli as well as the values of dynamic viscosity.

According to another aspect, the invention relates to an aerobic hyperhalophilic strain S3S1 deposited on 21 Feb. 2014 at the CNCM under the number CNCM I-4838.

According to another aspect, the invention relates to a use of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, for implementing a method for the degradation of a carbon-containing substrate comprising glucose.

According to another aspect, the invention relates to a use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation of a carbon-containing substrate comprising glucose.

According to another aspect, the invention relates to a use of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, for implementing a method for the degradation of a carbon-containing substrate in the absence of glucose.

According to an advantageous embodiment, the invention relates to a use as defined above, in which said method for the degradation of a carbon-containing substrate comprising glucose is implemented for preparing a biopolymer of the polyhydroxyalkanoate (PHA) type.

According to another aspect, the invention relates to a method for the degradation of a carbon-containing substrate such as oil, triglycerides, glycerol, fatty acids or derivatives thereof, comprising:
a growth step for an aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in a culture medium comprising glucose.

According to another aspect, the invention relates to a method for the degradation of a carbon-containing substrate such as oil, triglycerides, glycerol, fatty acids or derivatives thereof, comprising:
a growth step for an aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium comprising glucose.

According to another aspect, the invention relates to a method for the degradation of a carbon-containing substrate such as oil, triglycerides, glycerol, fatty acids or derivatives thereof, comprising:
a growth step for an aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in a culture medium in the absence of glucose.

According to another aspect, the invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1,
said culture being obtained after growth in a medium comprising glucose.

According to another aspect, the invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, said culture being obtained after growth in a medium comprising glucose.

According to another aspect, the invention relates to a method for the preparation of a biopolymer of the PHA type comprising:
(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%,
said culture being obtained after growth in a medium in the absence of glucose.

According to an advantageous embodiment, the invention relates to a method as defined above, comprising a growth step for an aerobic hyperhalophilic strain the whole genome of which has a percentage identity of at least 90%, 91%, 92%, 93%, 94%, 95%, 96%, 97%, 98% or 99% with the whole genome of said strain S3S1.

According to an advantageous embodiment, the invention relates to a method as defined above, comprising a growth step for an aerobic hyperhalophilic strain, being such that the percentage DNA-DNA hybridization between this aerobic hyperhalophilic strain and strain S3S1 is at least 90%, 91%, 92%, 93%, 94%, 95%, 96%, 97%, 98% or 99%.

According to an advantageous embodiment, the invention relates to a method as defined above, in which the culture medium comprises at least one salt.

According to an advantageous embodiment, the invention relates to a method as defined above, in which the salt is selected from NaCl, KCl, $CaCl_2$, $MgCl_2$, $MgSO_4$, hydrates thereof, in particular $CaCl_2.2H_2O$ and $MgCl_2.6H_2O$, and mixtures thereof.

According to an advantageous embodiment, the invention relates to a method as defined above, in which said salt is present in the culture medium at a concentration comprised from about 100 g/L to about 300 g/L, in particular from about 100 g/L to about 250 g/L.

According to an advantageous embodiment, the invention relates to a method as defined above, in which said strain is cultured in a medium in which the $NaCl/MgCl_2$ weight ratio is comprised from 15 to 100.

According to an advantageous embodiment, the invention relates to a method as defined above, in which said strain is cultured in a medium in which the $NaCl/CaCl_2$ weight ratio is comprised from 20 to 100.

According to an advantageous embodiment, the invention relates to a method as defined above, in which said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen.

According to an advantageous embodiment, the invention relates to a method as defined above, in which the ratio of carbon to nitrogen in the culture medium is comprised from 1 to 300.

According to an advantageous embodiment, the invention relates to a method as defined above, in which the ratio of carbon to phosphorus in the culture medium is comprised from 80 to 800.

According to an advantageous embodiment, the invention relates to a method as defined above, in which said strain is cultured in a medium in which:
the $NaCl/MgCl_2$ weight ratio is comprised from 15 to 100, and/or
the $NaCl/CaCl_2$ weight ratio is comprised from 20 to 100.

According to an advantageous embodiment, the invention relates to a method as defined above, in which:
said strain is cultured in a medium in which the $NaCl/MgCl_2$ weight ratio is comprised from 15 to 100, and/or the $NaCl/CaCl_2$ weight ratio is comprised from 20 to 100,
said strain is cultured under an atmosphere comprising less than 21% by volume of dioxygen, in particular less than 20%, 19%, 18%, 17%, 16%, 15%, 14%, 13%, 12%, 11%, 10%, 9%, 8%, 7%, 6%, 5%, 4%, 3%, 2% or 1% by volume of dioxygen,
the ratio of carbon to nitrogen in the culture medium is comprised from 1 to 300,
the ratio of carbon to phosphorus in the culture medium is comprised from 80 to 800.

According to an advantageous embodiment, the invention relates to a method as defined above, carried out under non-sterile conditions.

According to an advantageous embodiment, the invention relates to a method as defined above, carried out under non-sterile conditions, in which the culture medium comprises at least one salt, in particular selected from NaCl, KCl, $CaCl_2$, $MgCl_2$, $MgSO_4$, hydrates thereof, in particular $CaCl_2.2H_2O$ and $MgCl_2.6H_2O$, and mixtures thereof, said salt being present in the culture medium at a concentration comprised from about 100 g/L to about 300 g/L, in particular from about 100 g/L to about 250 g/L.

According to an advantageous embodiment, the invention relates to a method as defined above, in which the lysis step (a) comprises bringing said culture of said strain, optionally in the lyophilized form, into contact with a detergent in order to obtain a cellular lysate.

According to another advantageous embodiment, the invention relates to a method as defined above, in which the lysis step (a) comprises sonication of said culture of said strain in order to obtain a cellular lysate.

According to another advantageous embodiment, the invention relates to a method as defined above, in which the lysis step (a) comprises bringing said culture of said strain, optionally in the lyophilized form, into contact with a detergent, then sonication of the mixture thus obtained, in order to obtain a cellular lysate.

According to an advantageous embodiment, the invention relates to a method as defined above, in which step (b) of extraction of PHA is carried out
by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume,
in order to obtain said biopolymer of the PHA type and a cellular fraction.

According to an advantageous embodiment, the invention relates to a method as defined above comprising (c) a step of purification of the PHA.

According to a particularly advantageous embodiment, the invention relates to a method as defined above, in which said step of purification of the PHA is carried out by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction.

According to a particularly advantageous embodiment, the invention relates to a method as defined above, in which said step of purification of the PHA is carried out by washing said biopolymer of the PHA type and said cellular fraction with an organic solvent or a mixture of organic solvents, for example a mixture of acetone and ethanol, then adding an organic solvent, in particular chloroform, in particular at a temperature comprised from 20° C. to 80° C., more particularly at a temperature from 45° C. to 65° C., in order to obtain a solution of PHA in said organic solvent, said solution being devoid of the cellular fraction.

According to an advantageous embodiment, the invention relates to a method as defined above comprising:
(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in order to obtain a cellular lysate,
a step (b) of extraction of the PHA from the cellular lysate,
(c) a step of purification of the PHA.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in order to obtain a cellular lysate, a step (b) of extraction of the PHA from the cellular lysate, (c) a step of purification of the PHA.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in order to obtain a cellular lysate, said lysis step (a) comprising:
  bringing said culture of said strain, optionally in the lyophilized form, into contact with a detergent in order to obtain a cellular lysate,
  sonication of said culture of said strain in order to obtain a cellular lysate, or
  bringing said culture of said strain, optionally in the lyophilized form, into contact with a detergent, then sonication of the mixture thus obtained, in order to obtain a cellular lysate, a step (b) of extraction of the PHA from the cellular lysate, said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume, in order to obtain said biopolymer of the PHA type and a cellular fraction, (c) a step of purification of the PHA,
  said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain the whole genome of which has a percentage identity of at least 90%, in particular of at least 92%, with the whole genome of said strain S3S1, in order to obtain a cellular lysate, a step (b) of extraction of the PHA from the cellular lysate, (c) a step of purification of the PHA.

According to an advantageous embodiment, the invention relates to a method as defined above comprising:

(a) a step of lysis of a culture of the aerobic hyperhalophilic strain S3S1 deposited on 21 Feb. 2014 at the CNCM under the number CNCM I-4838, or of an aerobic hyperhalophilic strain being such that the percentage DNA-DNA hybridization between this aerobic hyperhalophilic strain and strain S3S1 is at least 90%, in particular at least 92%, in order to obtain a cellular lysate, said lysis step (a) comprising:
  bringing said culture of said strain, optionally in the lyophilized form, into contact with a detergent in order to obtain a cellular lysate,
  sonication of said culture of said strain in order to obtain a cellular lysate, or
  bringing said culture of said strain, optionally in the lyophilized form, into contact with a detergent, then sonication of the mixture thus obtained, in order to obtain a cellular lysate, a step (b) of extraction of the PHA from the cellular lysate, said step (b) of extraction of the PHA being carried out by precipitation by adding sodium hypochlorite, in particular sodium hypochlorite with at least 25%, in particular 30%, of active chlorine, to the cellular pellet obtained by centrifugation of the cellular lysate, in particular in a ratio of 1:1 volume by volume, in order to obtain said biopolymer of the PHA type and a cellular fraction, (c) a step of purification of the PHA,
  said step of purification of the PHA being carried out in particular by adding an organic solvent, in particular chloroform, in particular at a temperature comprised from 20° C. to 80° C., more particularly at a temperature from 45° C. to 65° C., to said biopolymer of the PHA type and to said cellular fraction, in order to obtain a solution of PHA in said organic solvent, said solution being devoid of the cellular fraction.

DETAILED DESCRIPTION

Examples

Figure 1:
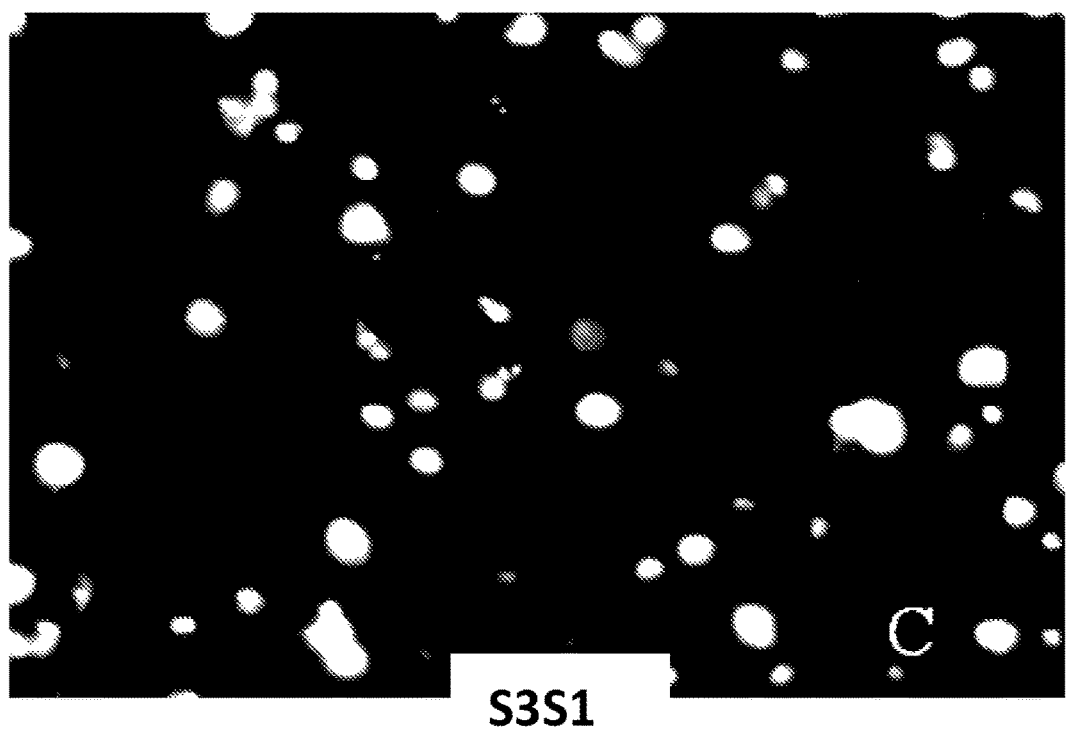
FIG. 1 illustrates an example of pigmentation with Nile red, showing the presence of PHA in strain S3S1.

Example 1: Degradation of a Carbon-Containing Substrate

The culture media used for degradation of the substrate defined below are for example of the following composition:
  $NH_4CL$, 1 g/L;
  KCl, 2 g/L;
  $CaCl_2.2H_2O$, 2 g/L;
  $MgCl_2.6H_2O$, 3 g/L;
  NaCl, 150 g/L;
  yeast extract, 1 g/L;
  substrate:
    (1) Glucose 2 g/L,
    (2) Glucose 2 g/L+10 g/L glycerol,
    (3) Glucose 2 g/L+10 g/L rapeseed oil,
    (4) Glucose 2 g/1+10 g/L of oleic acid,
    (5) Glycerol 10 g/L,
    (6) Rapeseed oil 10 g/L, or
    (7) Oleic acid 10 g/L.

The precultures were in particular carried out in penicillin bottles containing 50 ml of culture medium.

Larger volumes of culture medium (1.5 L, or even 2 L) were also used.

Culture was carried out in aerobiosis, at pH 7 and 37° C.

Example 1a: Production of PHA

Culture Media Used for Producing PHA:
The culture media used for producing PHA are for example of the following composition:
$NH_4CL$, 1 g/L;
KCl, 2 g/L;
$CaCl_2.2H_2O$, 2 g/L;
$MgCl_2.6H_2O$, 3 g/L;
NaCl, 150 g/L;
yeast extract, 1 g/L;
substrate:
- (1) Glucose 2 g/L,
- (2) Glucose 2 g/L+10 g/L glycerol,
- (3) Glucose 2 g/L+10 g/L rapeseed oil,
- (4) Glucose 2 g/L+10 g/L of oleic acid,
- (5) Glycerol 10 g/L,
- (6) Rapeseed oil 10 g/L, or
- (7) Oleic acid 10 g/L.

Higher concentrations of substrate may also be used.

The precultures were in particular carried out in penicillin bottles containing 50 ml of culture medium.

Larger volumes of culture medium (1.5 L, or even 2 L) were also used.

Culture was carried out in aerobiosis, at pH 7 and 37° C.

Detection of the Polyhydroxyalkanoates (PHAs)

Detection of PHAs in the S3S1 producing strain was carried out in particular on a medium containing 15% of NaCl; $NH_4Cl$, 1 g/l; KCl, 2 g/l; $CaCl_2.2H_2O$, 2 g/l; $MgCl_2.6H_2O$, 3 g/l; 10 g/l glycerol; 1 g/l of yeast extract, in the presence or in the absence of glucose. The pH of the medium is 7.0 and the growth temperature is 37° C.

A solution of Nile red 0.5 µg/ml, filtered and kept in the dark, was sprayed onto the strain with the aim of detecting the PHAs. Direct observation of the bacterial cells containing granules of PHA was carried out with a phase contrast microscope: Nikon Optiphot (Nikon, Tokyo, Japan) connected to a Nikon DS-FI 1 camera, and placed under fluorescence at 490 nm (FIG. 1).

Detection of the PHAs starting from a medium comprising rapeseed oil or oleic acid as substrate, in the presence or in the absence of glucose, was carried out in a similar manner.

Example 2: Extraction of PHA

Extraction of PHA was carried out starting from an isolate obtained in Example 1a, according to the following protocol:
- Lyophilize the bacterial culture (biomass) after recovery by centrifugation at 9000 rpm for 20 min;
- Add 5 ml of SDS (0.1%);
- Incubate for 24 h at 37° C. with stirring;
- Centrifuge the lysed suspension at 9000 rpm for 15 min, twice;
- Dissolve in sodium hypochlorite (30%);
- Incubate at 30° C. for 3 min;
- Centrifuge at 9000 rpm for 15 min;
- Discard the supernatant and wash the pellet with distilled water and then with an acetone/alcohol mixture (1:1);
- Vortex well;
- Dissolve in hot chloroform until evaporation occurs.

Results of the extraction of PHA, from cultures carried out in a large volume (1.5 L), comprising from 2.1 to 2.5 g of biomass, are shown in Table 1 below.

TABLE 1

| Substrate used | Quantity of PHA extracted (mg) |
|---|---|
| Rapeseed oil (6) | 90 |
| Rapeseed oil + Glucose (3) | 140 |
| Glycerol + Glucose (2) | 40 |
| Glucose (1) | 120 |

Example 3: Production of PHA without Sterilization of the Culture Medium

Growth of strain S3S1 could be obtained in a media comprising 150 or 200 g/L of NaCl, without autoclaving said media.

Example 4: Structure of the PHAs

The PHA obtained from substrate 3 (rapeseed oil+glucose, example 1a) was analysed by NMR, DSC and GPC.

Material and Methods

Analysis by NMR

The $^1H$ and $^{13}C$ NMR spectra are recorded in $CDCl_3$ (Bruker 400 MHz instrument).

Analysis by DSC

The thermal properties are determined by DSC (Diamond DSC—Perkin Elmer). The melting point is determined at the 1st passage and the glass transition temperature at the 2nd passage.

The temperature programme used is as follows:
1) from 20° C. to −50° C. at 40° C./min;
2) 3 min at −50° C.;
3) 1st passage: from −50° C. to 200° C. at 20° C./min;
4) from 180° C. to −50° C. at 200° C./min;
5) 3 min at −50° C.;
6) 2nd passage: −50° C. to 200° C. at 20° C./min.

Analysis by GPC

The samples are dissolved in chloroform (5 mg/mL) before analysis. Two methods of detection were used: the differential refractometer (RI) and light scattering (LS).

The molecular weights determined by RI are given in polystyrene equivalents.

The equipment used is as follows: the Shimadzu LC-20AD pump is equipped with 2 columns PL Gel Polymer Laboratories 5 µm mixed C and two detectors: a Wyatt Optilab Rex differential refractometer and a Wyatt Dawn Heleos 8 light scattering detector.

The polymers are analysed by light scattering using a do/dc of 0.034, a value that is characteristic of short side chain PHAs in chloroform.

Results

Analysis by DSC

The melting points (Mp) and the fusion enthalpies are determined at the 1st passage, and the glass transition temperatures (Tg) at the 2nd passage. The Tg is measured at the point of inflexion, and the Mp is measured at the top of the peak.

The exothermic peak is due to the phenomenon of crystallization and it appears during the 2nd passage.
The results are shown in Table 2.

TABLE 2

| Measurements carried out | Results |
|---|---|
| Tg (° C.) | +5 |
| Mp (° C.) | 157 |
| ΔHF (J/g) | 70 |

Determination of the Molecular Weights by SEC
The results for the number-average molecular weights Mn, the weight-average molecular weights Mw and the polymolecularity index PMI (sometimes called polydispersity index) are shown in Table 3.

TABLE 3

| | Measurements carried out | | | | | |
|---|---|---|---|---|---|---|
| | Mn(RI) | Mw(RI) | PDI(RI) | Mn(LS) | Mw(LS) | PMI(LS) |
| Results | 642 000 | 1 097 000 | 1.7 | 597 400 | 732 900 | 1.2 |

Figure 2:
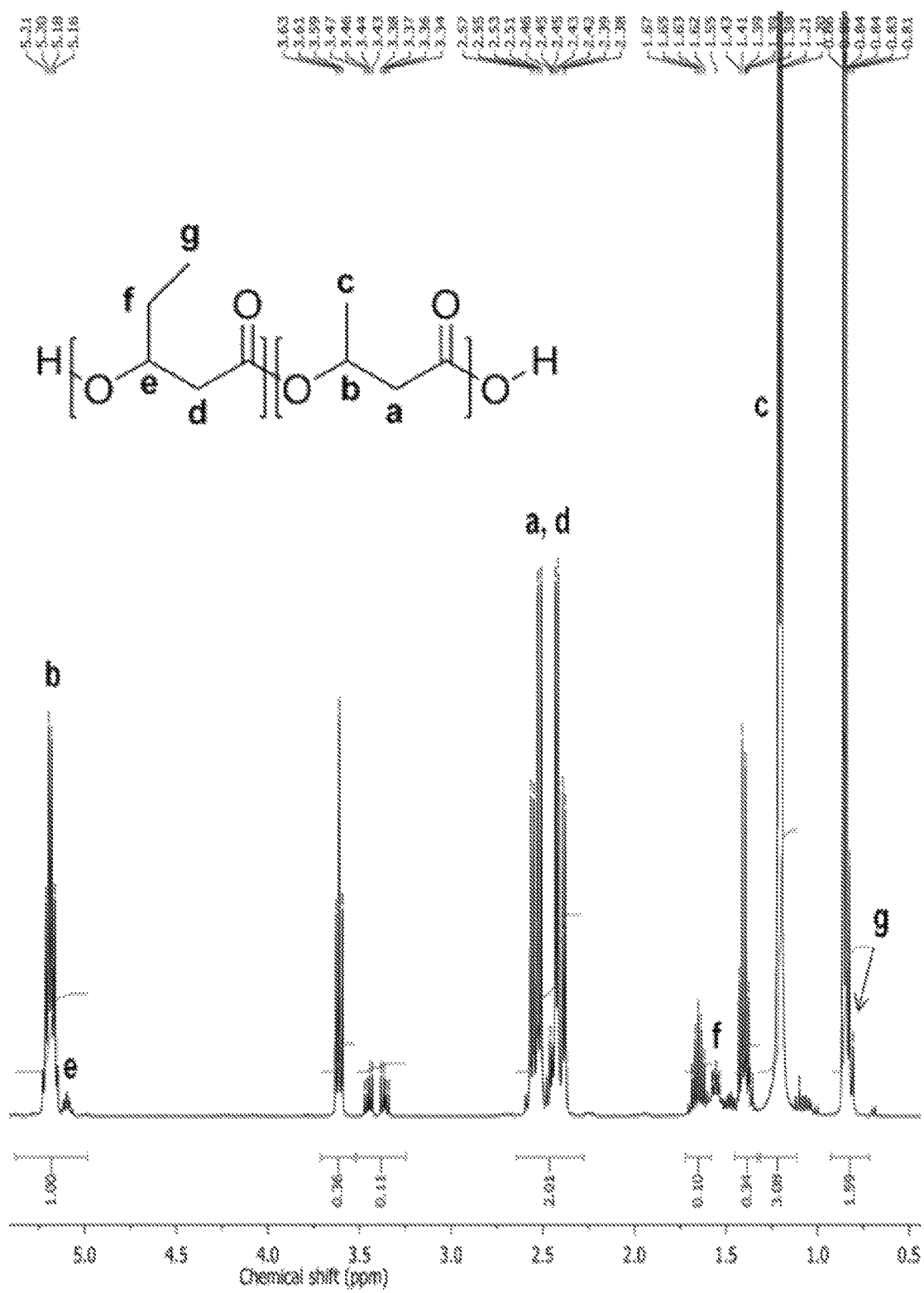
FIG. 2 shows the $^1$H NMR spectrum of the PHA obtained from substrate 3 (rapeseed oil+glucose, example 1a).
Figure 3:
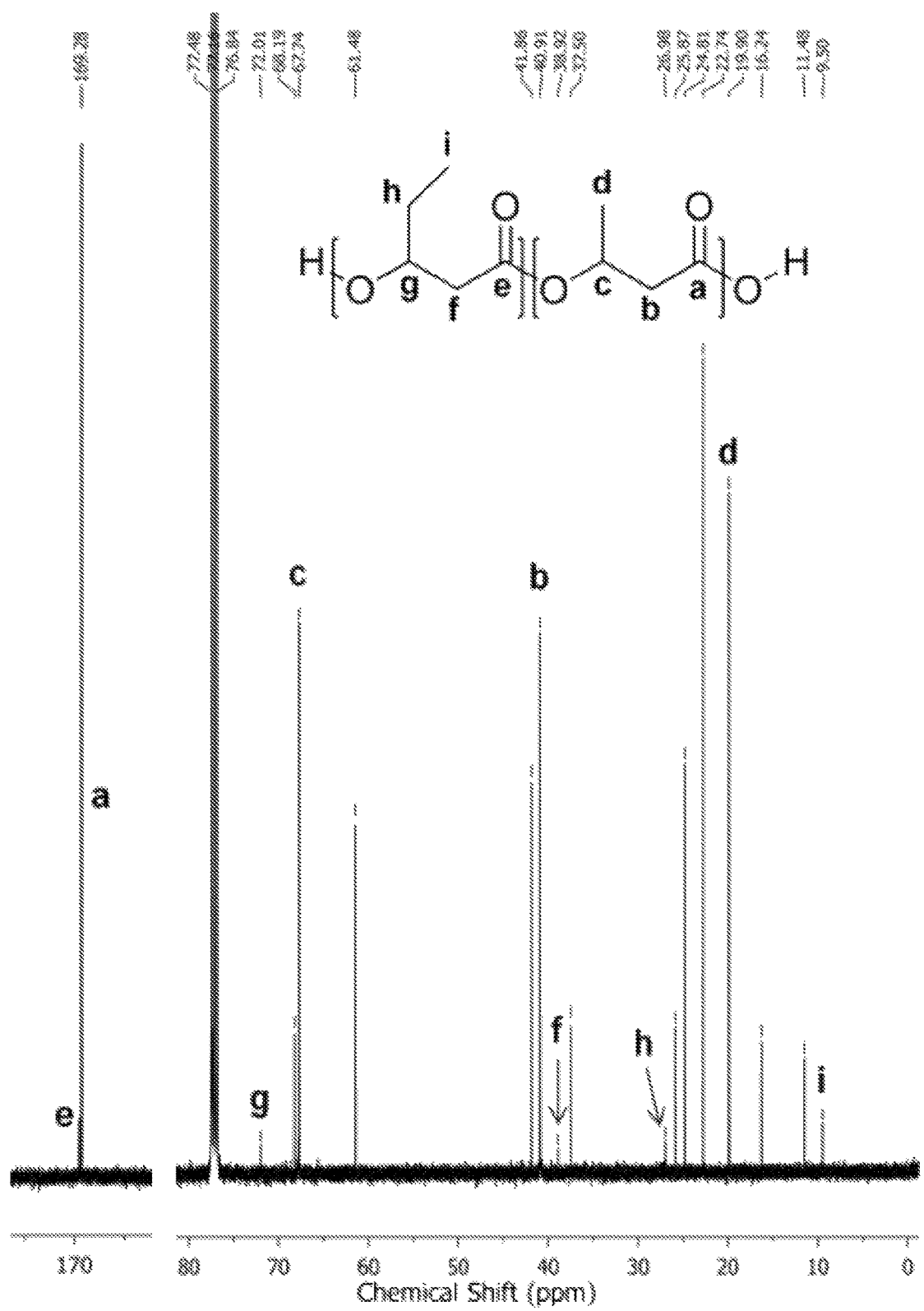
FIG. 3 shows the $^{13}$C NMR spectrum of the PHA obtained from substrate 3 (rapeseed oil+glucose, example 1a).

Determination of Chemical Structure by NMR
The $^1$H and $^{13}$C NMR spectra as well as the attributions are shown in FIGS. 2 and 3 respectively.
Conclusions
In proton NMR, the peaks at 1.2, 2.5 and 5.2 ppm are characteristic of the $CH_3$, $CH_2$ and CH groups, respectively, of poly(3-hydroxybutyrate), PHB (FIG. 2). These groups are also clearly identified by $^{13}$C NMR (19.6, 40.9 and 67.7 ppm). The peak at 169 ppm is also characteristic of the ester function (FIG. 3).

The sample consists predominantly of PHB. However, NMR indicates the presence of other groups in smaller quantities.

In $^1$H NMR, the peaks at 0.8, 1.5 and 5.05 are characteristic of the presence of hydroxyvalerate units (HV) ($CH_3$, $CH_2$ of the side chain and CH of the macromolecular backbone).

In $^{13}$C NMR, these groups can also be seen at 9.5, 27 and 72 ppm.

By finding the ratios of the integrations of the peaks located at 0.8 ppm (PHV) and at 1.2 ppm (PHB), it can be deduced that the proportion of HV units is 4%.

It is therefore a P(HB-co-HV) polymer in proportions 96/4.

This chemical structure is consistent with the results obtained in DSC, as the glass transition temperature Tg is 5° C. and the melting point Mp is 157° C., which is in agreement with the known results for the scl PHAs.

It should be noted, in connection with the behaviour of said polymer in solution, that said solution is perfectly clear but very viscous. The weight-average molecular weight determined by LS is particularly high (732 900 g/mol) and the polymolecularity index is 1.7 (Table 3).

The invention claimed is:
1. A method for degrading a hydrocarbon substrate, the method comprising the step of contacting the hydrocarbon substrate with an isolated hyperhalophilic aerobic strain comprising a genome having at least 90% DNA-DNA hybridization with the S3S1 strain deposited on Feb. 21, 2014 at the National Collection of Microorganisms Cultures (CNCM) under accession number CNCM I-4838 under conditions which cause the hyperhalophilic aerobic strain to degrade the hydrocarbon substrate and to produce polyhydroxyalkanoate (PHA), said hydrocarbon substrate being contained in the culture medium of said hyperhalophilic aerobic strain, wherein said hydrocarbon substrate is selected from the group consisting of a product or coproduct from an oil seed plant or from liquid hydrocarbons: a hydrocarbon selected from the group consisting of a triglyceride, an alkane, an alkene, a polyene, a fatty acid and glycerol, and mixture thereof; an animal oil; and a vegetable oil.

2. The method of claim 1, wherein the isolated hyperhalophilic aerobic strain is the S3S1 hyperhalophilic aerobic strain deposited on Feb. 21, 2014 at the National Collection of Microorganisms Cultures (CNCM) under accession number CNCM I-4838.

3. The method of claim 1, wherein said produced PHA has a weight-average molecular weight above 500,000 g/mol.

4. The method of claim 1, wherein the hydrocarbon substrate is a vegetable oil selected from the group consisting of rapeseed oil, sunflower oil, corn oil, linseed oil, olive oil, castor oil, soybean oil, palm oil, palm kernel oil, coconut oil, cottonseed oil, and groundnut oil and their mixtures.

5. The method of claim 1, wherein the hydrocarbon substrate comprises a hydrocarbon selected from the group consisting of a 6 to 24 carbon alkane, a 6 to 24 carbon alkene, a 6 to 24 carbon polyene, a 6-24 carbon fatty acid, and glycerol.

6. The method of claim 1, further comprising the step of contacting a carbohydrate co-substrate with the hyperhalophilic aerobic strain.

7. The method of claim 6, wherein the carbohydrate co-substrate is glucose.

8. The method of claim 1, wherein the step of contacting the hydrocarbon substrate with the isolated hyperhalophilic aerobic strain is performed in a culture medium comprising at least one salt selected from the group consisting of NaCl, KCl, $CaCl_2$, $MgCl_2$, $MgSO_4$, and hydrates thereof and their mixtures.

9. The method of claim 8, wherein the at least one salt is selected from the group consisting of a $NaCl/MgCl_2$ mixture with a weight ratio of 15 to 100, and a $NaCl/CaCl_2$ mixture with a weight ratio of 20 to 100.

10. The method of claim 1, wherein the step of contacting the hydrocarbon substrate with the isolated hyperhalophilic aerobic strain is performed under an atmosphere comprising less than 21% by volume of oxygen.

11. The method of claim 8, wherein the culture medium comprises nitrogen and carbon in a ratio of 1 to 300.

12. The method of claim 8, wherein the culture medium comprises phosphorus and carbon in a ratio of 80 to 800.

13. A method for preparing a PHA, the method comprising the steps of:
(a) culturing an isolated hyperhalophilic aerobic strain comprising a genome having at least 90% DNA-DNA hybridization with the S3S1 hyperhalophilic aerobic strain deposited on Feb. 21, 2014 at the National Collection of Microorganisms Cultures (CNCM) under accession number CNCM I-4838 in a culture medium comprising a hydrocarbon substrate under conditions which cause the strain to produce the PHA, wherein said hydrocarbon substrate is selected from the group consisting of a product or coproduct from an oil seed plant or from liquid hydrocarbons: a hydrocarbon selected from the group consisting of a triglyceride, an alkane, an alkene, a polyene, a fatty acid and glycerol, and mixture thereofo; an animal oil; and a vegetable oil;

(b) lysing the cultured hyperhalophilic aerobic strain to create a cell lysate; and (c) extracting the PHA from the cell lysate.

14. The method of claim 13, wherein the step of lysing the cultured hyperhalophilic aerobic strain to create a cell lysate is performed by a lysis method selected from the group consisting of: contacting the cultured hyperhalophilic aerobic strain with a detergent, sonicating the cultured hyperhalophilic aerobic strain, and sonicating the cultured hyperhalophilic aerobic strain in the presence of a detergent.

15. The method of claim 13, wherein the step of extracting the PHA from the cell lysate comprises adding sodium hypochlorite to the cell lysate to precipitate out the PHA and a cell fraction.

16. The method of claim 13, wherein the step of extracting the PHA from the cell lysate comprises adding sodium hypochlorite to the cell lysate to precipitate out the PHA and a cell fraction and comprising d) purifying the PHA which comprises adding an organic solvent to the PHA and to the cell fraction, to obtain a liquid fraction comprising the PHA devoid of the cell fraction.

17. An isolated and lyophilized hyperhalophilic aerobic strain able to degrade a hydrocarbon substrate and produce PHA, the strain comprising a genome having at least 90% DNA-DNA hybridization with the S3S1 hyperhalophilic aerobic strain deposited on Feb. 21, 2014 at the National Collection of Microorganisms Cultures (CNCM) under accession number CNCM I-4838, in particular said strain is the S3S1 hyperhalophilic aerobic strain deposited on Feb. 21, 2014 at the National Collection of Microorganisms Cultures (CNCM) under accession number CNCM I-4838.

* * * * *